(12) United States Patent
Shin et al.

(10) Patent No.: US 8,398,699 B2
(45) Date of Patent: Mar. 19, 2013

(54) DRAWSTRING FOR REMOVAL OF STENT

(75) Inventors: Kyong-Min Shin, Seoul (KR);
Byung-Cheol Myung, Kyongki-do (KR); Sung-Min Kim, Seoul (KR);
Yong-Hyun Won, Incheon-si (KR)

(73) Assignees: Taewoong Medical Co., Ltd., Kyunggi-do (KR); Kyong-Min Shin, Seoul (KR)

( * ) Notice: Subject to any disclaimer, the term of this patent is extended or adjusted under 35 U.S.C. 154(b) by 167 days.

(21) Appl. No.: 12/770,491

(22) Filed: Apr. 29, 2010

(65) Prior Publication Data
US 2010/0280591 A1 Nov. 4, 2010

(30) Foreign Application Priority Data

Apr. 30, 2009 (KR) .................. 10-2009-0037988

(51) Int. Cl.
*A61F 2/06* (2006.01)
*A61M 29/00* (2006.01)
(52) U.S. Cl. ...................... 623/1.11; 606/198
(58) Field of Classification Search .................. 606/194, 606/195, 198; 623/1.11–1.16, 1.23, 1.34, 623/1.38, 1.42
See application file for complete search history.

(56) References Cited

U.S. PATENT DOCUMENTS

| 5,653,748 A * | 8/1997 | Strecker ........................ 623/1.11 |
| 5,873,906 A * | 2/1999 | Lau et al. ........................ 128/898 |
| 6,340,367 B1 * | 1/2002 | Stinson et al. ............... 623/1.34 |
| 2002/0007208 A1 * | 1/2002 | Strecker ........................ 623/1.12 |

* cited by examiner

*Primary Examiner* — Tuan V Nguyen
(74) *Attorney, Agent, or Firm* — IP & T Group LLP

(57) ABSTRACT

A stent system includes a stent and a drawstring for removal of the stent.

The drawstring includes an end string, a longitudinal string and a circumferential string. The end string is formed in an end of the stent body in an annular shape in such a way that the end string passes, in a zigzag manner, through mesh arranged in a circumferential direction of the stent body. A hook loop is formed by tying opposite ends of the end string to each other. The longitudinal string extends at a first end thereof from the end string in the longitudinal direction of the stent body. The circumferential string extends from a second end of the longitudinal string and is formed in an annular shape in such a way that the circumferential string passes, in a zigzag manner, through mesh arranged in the circumferential direction of the stent body.

14 Claims, 24 Drawing Sheets lesion portion lesion portion

DRAWSTRING FOR REMOVAL OF STENT

BACKGROUND OF THE INVENTION

1. Field of the Invention

The present invention relates generally to drawstrings for removal of stents and, more particularly, to a drawstring for removal of a stent which is configured such that when the drawstring is pulled by a stent removal device to remove the stent from a lumen, for example, to conduct reoperation, the stent is extended in a longitudinal direction and contracted in diameter by the drawstring, so that the stent which has been grasped by the inner wall of the lumen can be easily separated therefrom, thus facilitating the removal of the stent.

2. Description of the Related Art

Generally, a medical stent is used to expand a lumen which has contracted in diameter or to prevent expanded lumens from contracting.

In other words, medical stents functions to expand a lumen which has contracted, for example, by the occurrence of a tumor such as cancer, or to prevent the progression of contraction of a lumen.

For instance, such a medical stent is used to cope with the contraction of a pancreatic duct because of acute pancreatitis, the contraction of a bile duct attributable to chronic cholangitis, the temporary contraction of a lumen occurring after surgery, etc. Particularly, the medical stent which has been used to prevent symptoms of the temporary contraction of a lumen or to expand a contracted lumen is removed from the lumen after the lumen has recovered its original state. In addition, when the stent is placed in the lumen at an incorrect position and thus does not function as normal or is rendered ineffectual, the stent which has been placed in the lumen must be removed therefrom before reoperation can be conducted.

Typically, the stent which can be removed is inserted into a lumen by a well-known catheter to prevent contraction of the lumen or expand the diameter of the lumen. When the stent is removed from the lumen, if a leading and of the stent with respect to the direction in which the stent is extracted can be contracted in diameter, the removal of the stent is facilitated.

Preferably, the stent is configured such that it can be removed from the lumen using a hook of a stent removal device. With regard to the structure for removal of the stent, a plurality of loops is integrally connected to a stent body and to a cover which covers the inner and outer surfaces of the stent body. In addition, at least one string is connected at both ends thereof to each loop.

Therefore, to remove the stent from the lumen, the hook is inserted into the stent body and moved forwards and backwards until it becomes hooked to one loop. Thereafter, the hook is pulled. Then, the stent contracts towards the central axis thereof.

When the hook is further pulled, the stent body is inserted into a tube of the stent removal device. Subsequently, the stent is completely removed from the lumen by removing the tube and the hook from the lumen together.

As shown in FIGS. 1 and 2, in the conventional stent having the above-mentioned structure, the stent is extracted from the lumen in such a way that the hook is hooked to one of the loops and pulled. However, when the stent is pulled by the hook, the pulling force is concentrated on only a portion of the circumference of the stent. Thereby, although the stent is extended in length, a ratio of reduction in the diameter of the stent is relatively low, thus making the extraction of the stent from the lumen difficult.

Furthermore, when the stent remains in the lumen for a long period of time, a lesion portion or lumen tissue may become stuck or attached to the stent. In this case, the stent is not easily extracted from the lumen by the pulling force. Rather, the lesion portion or lumen tissue is pulled along with the stent, thus resulting in the recurrence of a lesion or pain to a patient.

In addition, regardless of an area of the lesion portion, the loops are provided only on the end of the stent. Hence, when one of the loops is pulled, the pulling force is concentrated on the end of the stent but may not be transmitted to the portion of the stent to which the lesion portion is stuck or attached, so that the removal of the stent becomes difficult.

Therefore, a drawstring for removal of a stent is required, which is configured such that when a loop is pulled, the pulling force is transmitted to the entire stent and simultaneously the diameter of the stent is reduced so that the stent can be easily removed from a lumen, even when it is in a state of being grasped by the inner wall of the lumen.

SUMMARY OF THE INVENTION

Accordingly, the present invention has been made keeping in mind the above problems occurring in the prior art, and an object of the present invention is to provide a drawstring for removal of a stent which is configured such that even if an inner wall of a lumen penetrates into the mesh of the stent and is attached thereto, the stent can be easily separated from the lumen by reducing the diameter of the stent.

Another object of the present invention is to provide a drawstring which includes an end string, a longitudinal string and a circumferential string so that when the end string is pulled, the stent is extended in a longitudinal direction and simultaneously contracted in diameter, so that the stent is easily separated from the inner wall of the lumen.

A further object of the present invention is to provide a drawstring which can be manufactured in various shapes depending on the shape or characteristics of the stent to increase the compatibility.

Yet another object of the present invention is to provide a drawstring in which the length of the longitudinal string or a distance between circumferential strings can be adjusted depending on an area of a lesion portion in the lumen or on the length of the stent, such that when the drawstring is pulled to remove the stent, a ratio of contraction of the stent is relatively uniform over the entire length of the stent.

In order to accomplish the above object, the present invention provides a drawstring for removal of a stent, the stent having a cylindrical stent body formed by weaving at least one strand of a shape memory alloy wire such that mesh is defined by the wire and bent portions are formed along circumferences of opposite ends of the stent body. The drawstring includes: an end string formed in an end of the stent body in an annular shape in such a way that the end string passes, in a zigzag manner, through mesh arranged in a circumferential direction of the stent body, with a hook loop formed by tying opposite ends of the end string to each other; a longitudinal string extending at a first end thereof from the end string, the longitudinal string being inserted into the stent body through a mesh, and extending a predetermined length through an interior of the stent body, and coming out of the stent body through another mesh; a circumferential string extending from a second end of the longitudinal string, the circumferential string being formed in an annular shape in such a way that the circumferential string passes, in a zigzag manner, through mesh arranged in the circumferential direction of the stent body.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, a preferred embodiment of the present invention will be described in detail with reference to the attached drawings.

Figure 1:
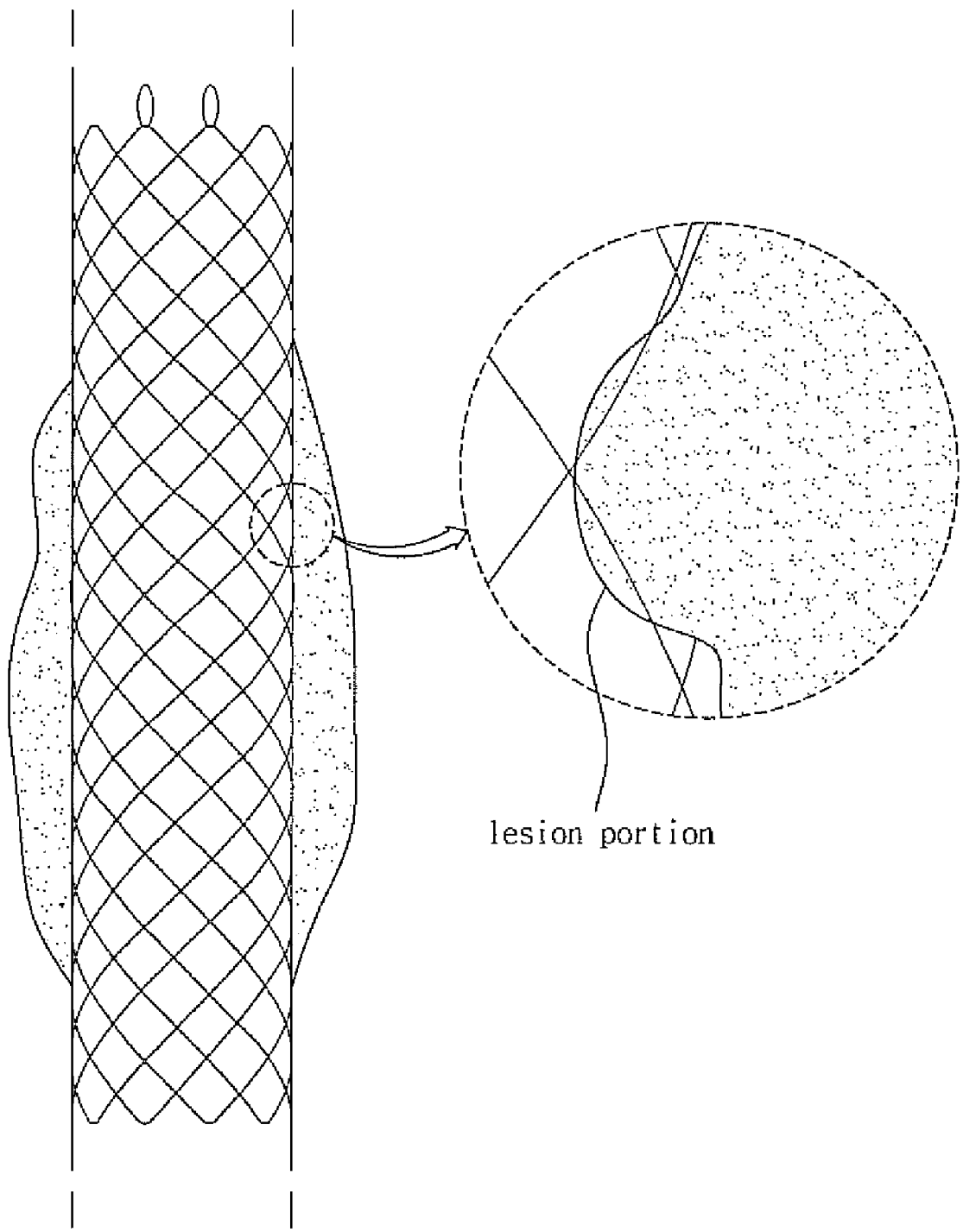
FIG. 1 is of a view showing a stent placed on a lesion portion and an enlarged sectional view showing lumen tissue which has penetrated into the mesh of the stent, according to a conventional technique.
Figure 2:
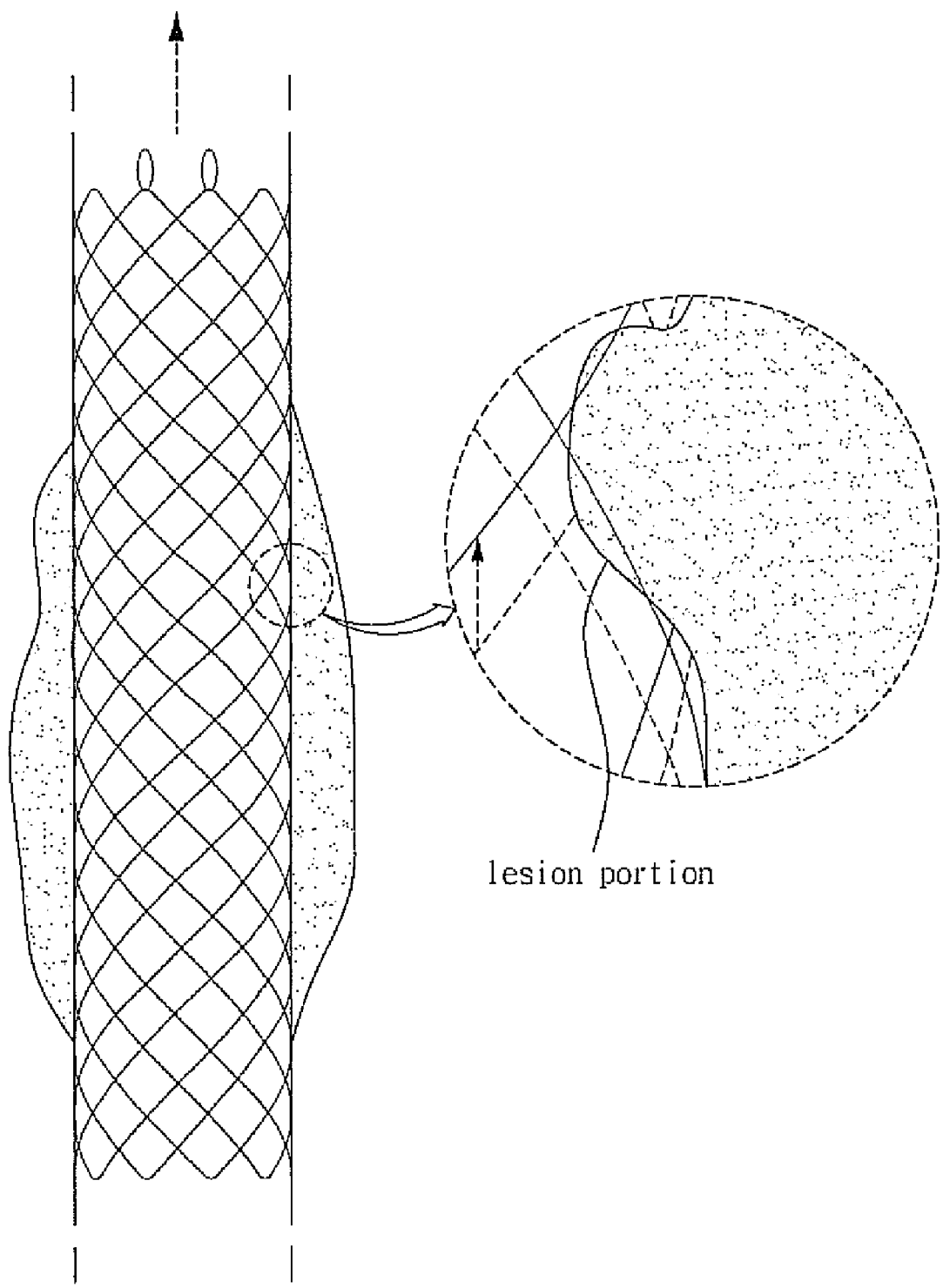
FIG. 2 is of a schematic view and an enlarged sectional view showing the conventional stent stuck to the lumen tissue which has penetrated into the mesh of the stent when an operation of removing the stent is conducted.
Figure 3:
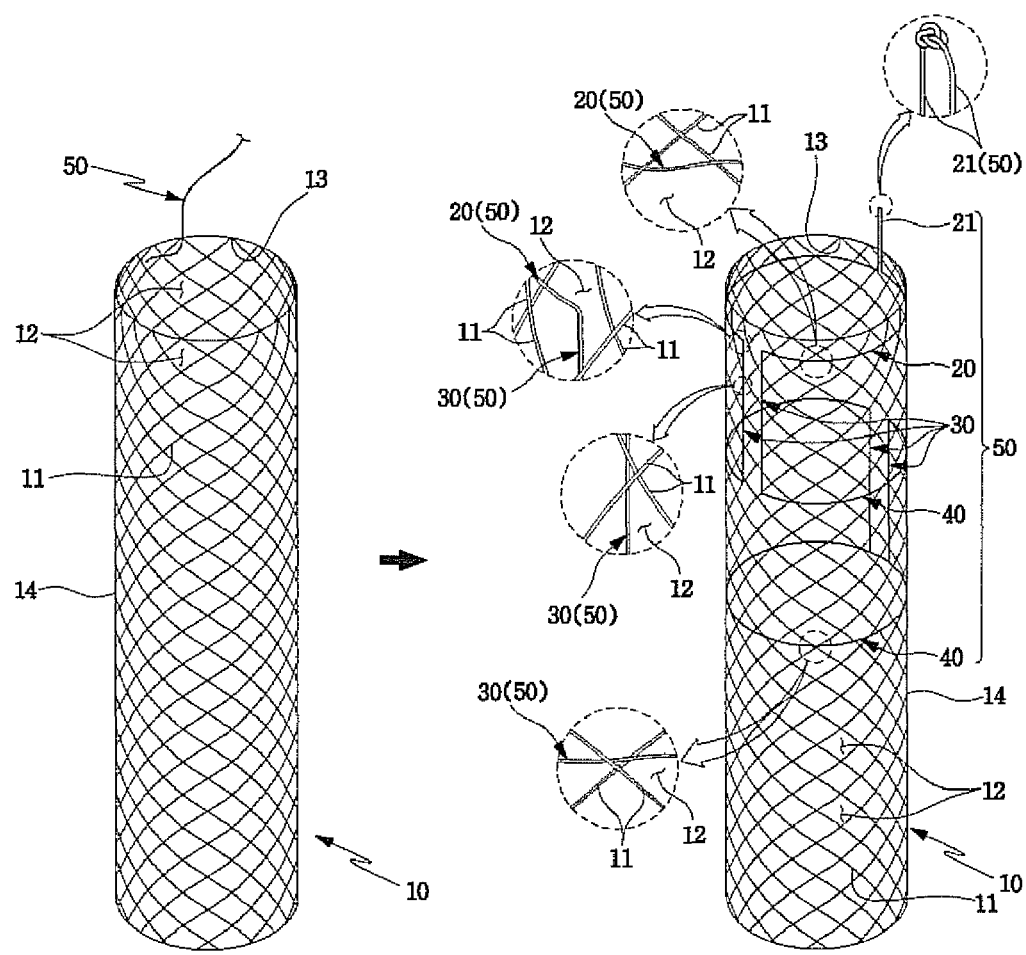
FIG. 3 is of a perspective view of a stent and a perspective view showing a drawstring provided in the stent, according to a first embodiment of the present invention.
Figure 4:
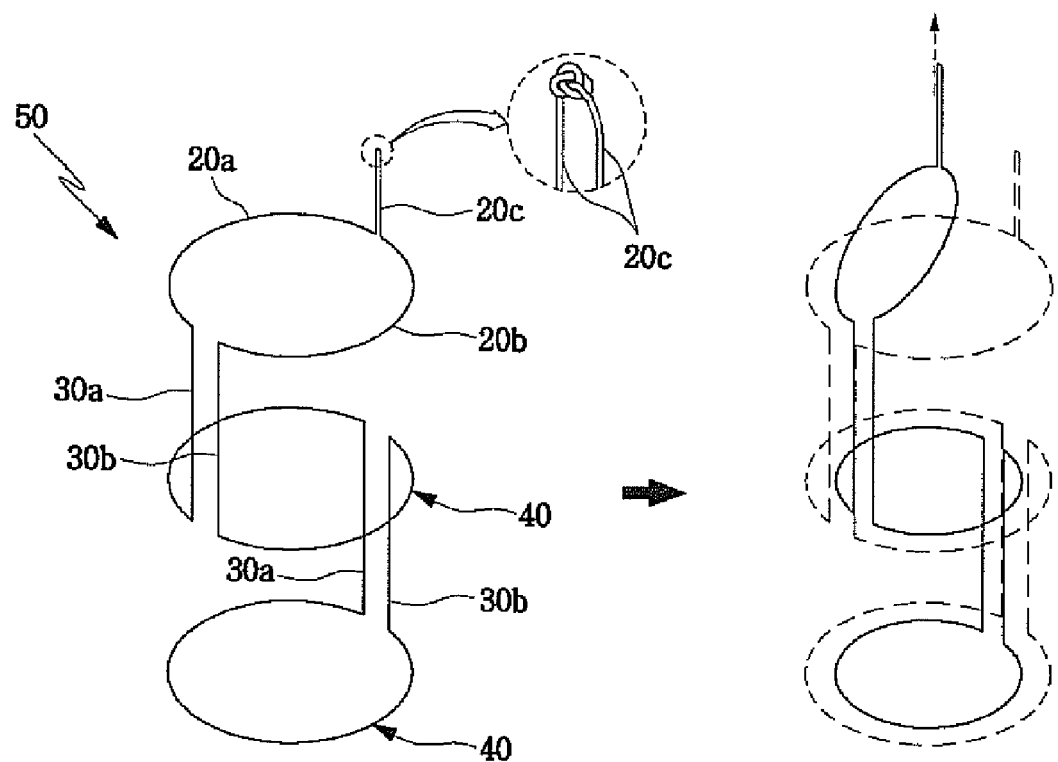
FIG. 4 is of perspective views showing the shape and operation of the drawstring of FIG. 3.

As shown in FIGS. 3 and 4, the present invention provides a drawstring 50 for removal of a stent 10. The stent 10 includes a cylindrical stent body 14 which is manufactured by weaving one or more strands of shape memory alloy wires 11 or crossing them with each other in a zigzag manner such that mesh 12 is defined by the wires 11 and bent portions 13 are formed along the circumferences of both ends of the cylindrical stent body 14. The drawstring 50 has an end string 20 which is formed on one end of the cylindrical stent body 14 into an annular shape in such a way that it is threaded into the corresponding mesh 12 of the cylindrical stent body 14 in a zigzag manner. A hook loop 21 is formed by tying both ends of the end string 20.

Furthermore, a longitudinal string 30 integrally extends from the end string 30 or a first end of the longitudinal string 30 is tied to the end string 30. The longitudinal string 30 is threaded through corresponding mesh 12 which is arranged with respect to the longitudinal direction of the cylindrical stent body 14, in such a way that the longitudinal string 30 is inserted into the cylindrical stent body 14 through one corresponding mesh 12, extends a predetermined length through the interior of the stent body 14, and comes out of the stent body 14 through another mesh 12.

In addition, at least one circumferential string 40 having an annular shape is formed in a predetermined portion of the cylindrical stent body 14 in such a way that the circumferential string 40 is threaded, in a zigzag manner, into mesh 12 which is disposed in the circumferential direction of the cylindrical stent body 14. The circumferential string 40 integrally extends from a second end of the longitudinal string 30 or is tied thereto. In the present invention, the stent 10 having the drawstring 50 can be configured in the above-mentioned manner.

In the stent 10, when the hook loop 21 is pulled, the end string 20, the longitudinal string 30 and the circumferential string 40 are pulled in consecutive order. Here, the end string 20 is pulled in the diametrical and longitudinal directions of the cylindrical stent body 14. The longitudinal string 30 is pulled in the longitudinal direction of the cylindrical stent body 14. The circumferential string 40 is pulled in the diametrical direction of the cylindrical stent body 14. As a result, the stent 10 can be easily separated from the inner surface of a lumen in the patients' body.

1. As shown in FIG. 4, the drawstring 50 according to a first embodiment of the present invention integrally includes a first end string 20a, a first longitudinal string 30a, a circumferential string 40, a second longitudinal string 30b and a second end string 20b.

The first end string 20a is woven with the cylindrical stent body 14 of the stent 10 to form a semicircular shape in such a way that the first end string 20a is threaded into corresponding mesh 12 of the cylindrical stent body 14 in a zigzag manner.

The first longitudinal string 30a extends at a first end thereof from a second end of the first end string 20a and passes through corresponding mesh 12 which is arranged with respect to the longitudinal direction of the cylindrical stent body 14, in such a way that the first longitudinal string 30a is inserted into the cylindrical stent body 14 through one corresponding mesh 12, extends a predetermined length through the interior of the stent body 14, and comes out of the stent body 14 through another mesh 12.

At a first end thereof, the circumferential string 40 is integrally extended from a second end of the first longitudinal string 30a and is woven through corresponding mesh 12 which is arranged in the circumferential direction of the cylindrical stent body 14. The circumferential string 40 may comprise one or more circumferential strings 40 which have a semicircular shape and/or a circular shape.

At a first end of the second longitudinal string 30b, the second longitudinal string 30b integrally extends from a second end of the circumferential string 40 such that the second longitudinal string 30b is parallel to the first longitudinal string 30a. The second end string 20b integrally extends at a first end thereof from a second end of the second longitudinal string 30b such that the second end string 20b is symmetrical with the first end string 20a. Thereafter, a hook loop 20c is formed by tying a second end of the second end string 20b to the first end of the first end string 20a.

As such, the drawstring 50 of the first embodiment is configured such that the first end string 20a, the first longitudinal string 30a, the circumferential string 40, the second longitudinal string 30b and the second end string 20b are integrally formed into a single string.

Figure 5:
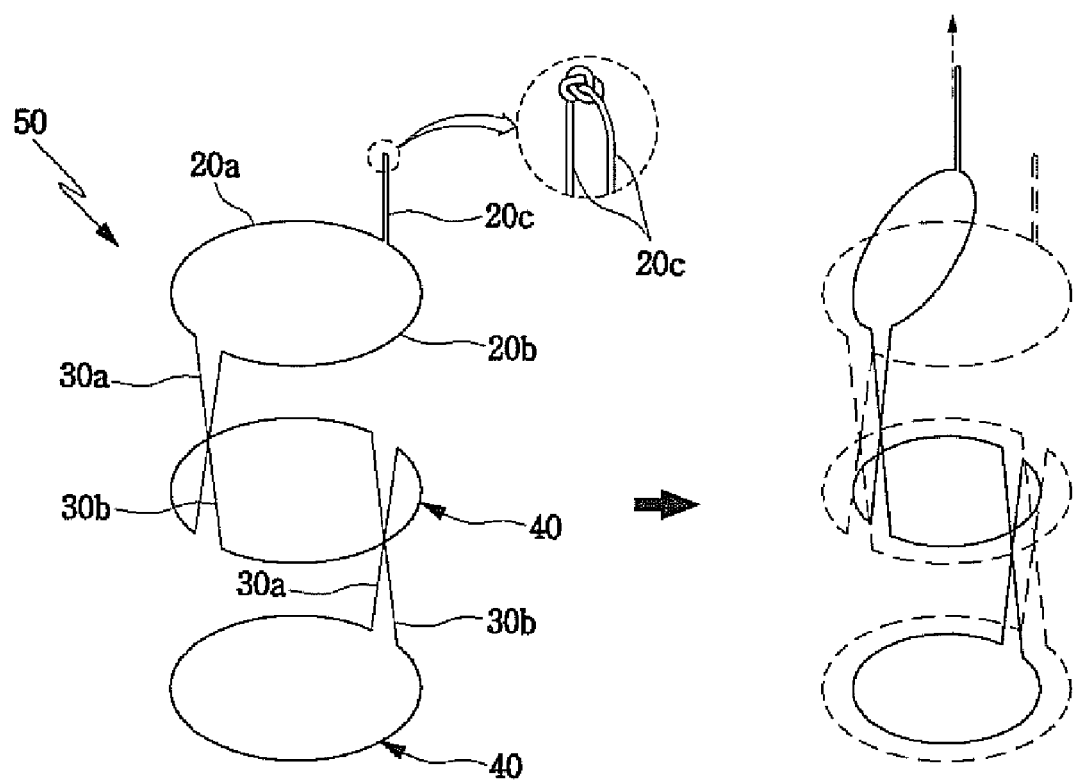
FIG. 5 is of perspective views showing the shape and operation of a drawstring, according to a second embodiment of the present invention.

2. As shown in FIG. 5, the drawstring 50 according to a second embodiment of the present invention integrally includes a first end string 20a, a first longitudinal string 30a, a circumferential string 40, a second longitudinal string 30b and a second end string 20b.

The first end string 20a is woven with the cylindrical stent body 14 of the stent 10 to form a semicircular shape in such a way that the first end string 20a is threaded into corresponding mesh 12 of the cylindrical stent body 14 in a zigzag manner.

The first longitudinal string 30a extends at a first end thereof from a second end of the first end string 20a and passes through corresponding mesh 12 which is arranged with respect to the longitudinal direction of the cylindrical stent body 14, in such a way that the first longitudinal string 30a is inserted into the cylindrical stent body 14 through one corresponding mesh 12, extends a predetermined length through the interior of the stent body 14, and comes out of the stent body 14 through another mesh 12.

The circumferential string 40 integrally extends at a first end thereof from a second end of the first longitudinal string 30a and is woven through corresponding mesh 12 which is arranged in the circumferential direction of the cylindrical stent body 14. The circumferential string 40 may comprise one or more circumferential strings 40 which have a circular shape.

The second longitudinal string 30b integrally extends at a first end thereof from a second end of the circumferential string 40 such that the second longitudinal string 30b and the first longitudinal string 30a cross over each other. The second end string 20b integrally extends at a first end thereof from a second end of the second longitudinal string 30b such that the second end string 20b is symmetrical with the first end string 20a. Thereafter, a hook loop 20c is formed by tying a second end of the second end string 20b to the first end of the first end string 20a.

Figure 6:
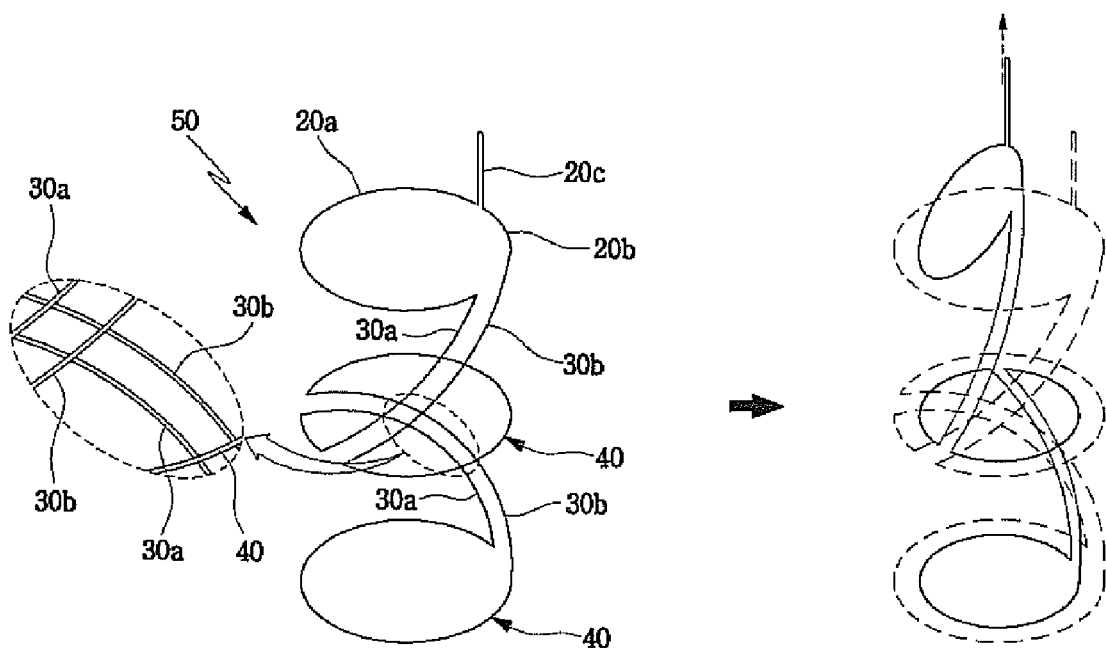
FIG. 6 is of perspective views showing the shape and operation of a drawstring, according to a third embodiment of the present invention.

3. As shown in FIG. 6, the drawstring 50 according to a third embodiment of the present invention integrally includes a first end string 20a, a first longitudinal string 30a, a circumferential string 40, a second longitudinal string 30b and a second end string 20b.

The first end string 20a is woven with the cylindrical stent body 14 of the stent 10 to form a semicircular shape in such a way that the first end string 20a is threaded into corresponding mesh 12 of the cylindrical stent body 14 in a zigzag manner.

The first longitudinal string 30a extends at a first end thereof from a second end of the first end string 20a and passes through corresponding mesh 12 which is arranged with respect to the diagonal direction of the cylindrical stent body 14, in such a way that the first longitudinal string 30a is inserted into the cylindrical stent body 14 through one corresponding mesh 12, extends a predetermined length through the interior of the stent body 14, and comes out of the stent body 14 through another mesh 12.

The circumferential string 40 integrally extends at a first end thereof from a second end of the first longitudinal string 30a and is woven through corresponding mesh 12 which is arranged in the circumferential direction of the cylindrical stent body 14. The circumferential string 40 may comprise one or more circumferential strings 40 which have a circular shape.

The second longitudinal string 30b extends at a first end thereof from a second end of the circumferential string 40 and is woven through corresponding mesh 12 in a zigzag manner such that the second longitudinal string 30b crosses over the first longitudinal string 30a.

The second end string 20b extends at a first end thereof from a second end of the second longitudinal string 30b and is configured such that the second end string 20b faces and is spaced apart from the first end string 20a. Thereafter, a hook loop 20c is formed by tying a second end of the second end string 20b to the first end of the first end string 20a.

As such, the drawstring 50 of the third embodiment is configured such that the first end string 20a, the first longitudinal string 30a, the circumferential string 40, the second longitudinal string 30b and the second end string 20b are integrally formed into a single string.

Figure 7:
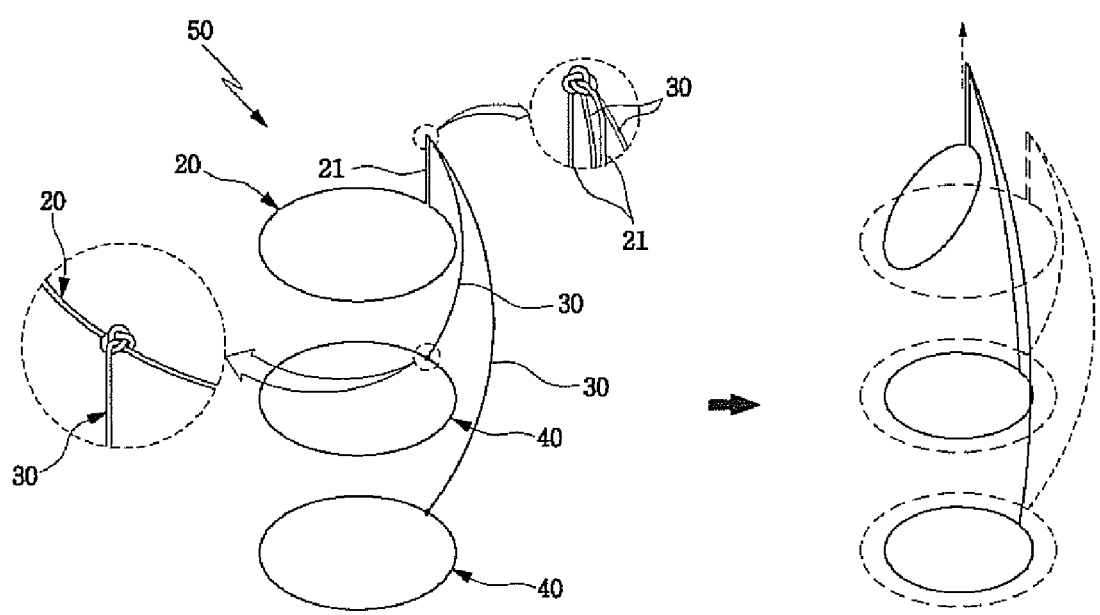
FIG. 7 is of perspective views showing the shape and operation of a drawstring, according to a fourth embodiment of the present invention.

4. As shown in FIG. 7, in the drawstring 50 according to a fourth embodiment of the present invention, an end string 20 is woven with the cylindrical stent body 14 of the stent 10 to form a circular shape in such a way that the end string 20 is threaded into corresponding mesh 12 of the cylindrical stent body 14 in a zigzag manner. A hook loop 21 is formed by tying both ends of the end string 20 to each other.

One or more longitudinal strings 30 are tied at first ends thereof to the hook loop 21 of the end string 20. Each longitudinal string 30 passes through corresponding mesh 12 which is arranged with respect to the longitudinal direction of the cylindrical stent body 14, in such a way that the longitudinal string 30 is inserted into the cylindrical stent body 14 through one corresponding mesh 12, extends a predetermined length through the interior of the stent body 14, and comes out of the stent body 14 through another mesh 12.

Furthermore, one or more circumferential strings 40 are woven with the cylindrical stent body 14 into circular shapes through corresponding mesh 12 which is arranged in the circumferential direction of the cylindrical stent body 14. Each circumferential string 40 is tied to a second end of the corresponding longitudinal string 30.

Figure 8:
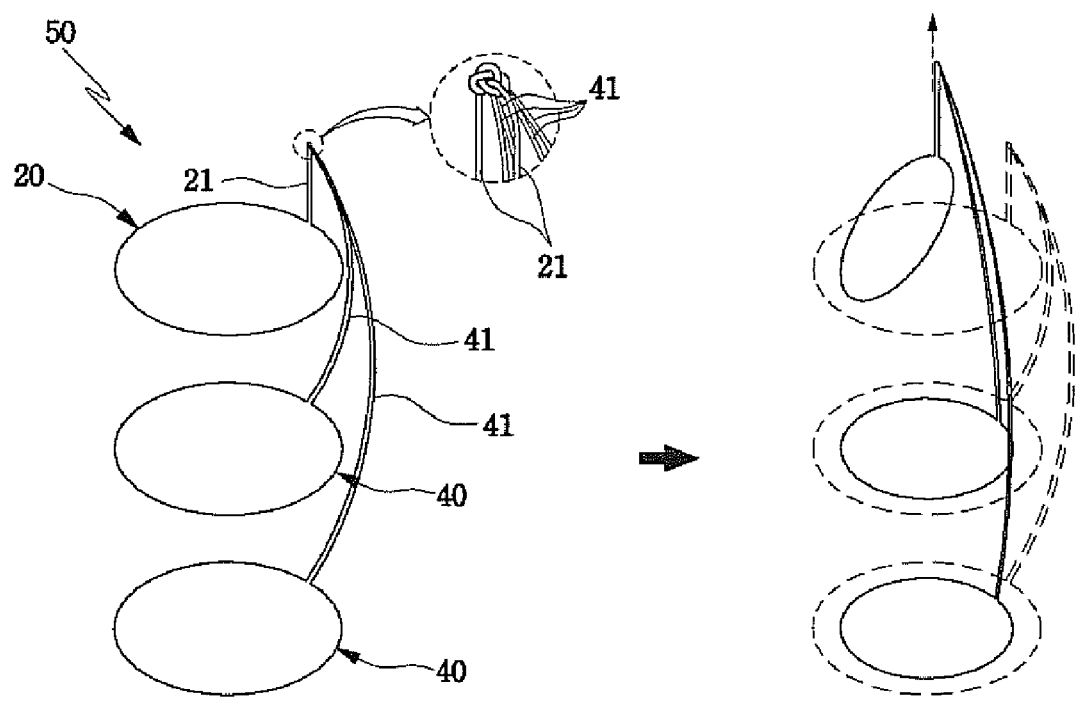
FIG. 8 is of perspective views showing the shape and operation of a drawstring, according to a fifth embodiment of the present invention.

5. As shown in FIG. 8, in the drawstring 50 according to a fifth embodiment of the present invention, an end string 20 is woven with the cylindrical stent body 14 of the stent 10 to form a circular shape in such a way that the end string 20 is threaded into corresponding mesh 12 of the cylindrical stent body 14 in a zigzag manner. A hook loop 21 is formed by tying both ends of the end string 20 to each other.

Furthermore, one or more circumferential strings 40 are woven with the cylindrical stent body 14 into circular shapes through corresponding mesh 12 which is arranged in the circumferential direction of the cylindrical stent body 14. Both ends of each circumferential string 40 are tied to each other to form a tie loop 41. The tie loops 41 of the circumferential strings 40 are tied to the hook loop 21 of the end string 20.

Figure 9:
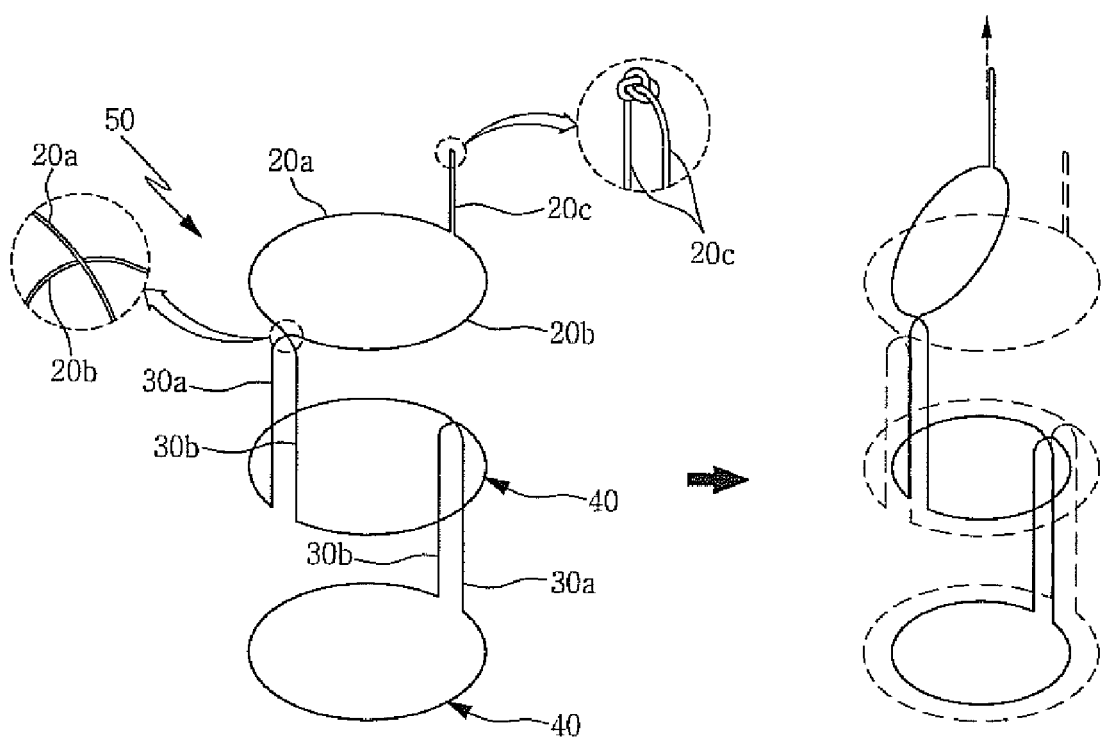
FIG. 9 is of perspective views showing the shape and operation of a drawstring, according to a sixth embodiment of the present invention.

6. As shown in FIG. 9, in the drawstring 50 according to a sixth embodiment of the present invention, a first end string 20a is woven with the cylindrical stent body 14 of the stent 10 to form a semicircular shape in such a way that the first end string 20a is threaded into corresponding mesh 12 of the cylindrical stent body 14 in a zigzag manner.

The first longitudinal string 30a extends at a first end thereof from a second end of the first end string 20a and passes through corresponding mesh 12 which is arranged with respect to the longitudinal direction of the cylindrical stent body 14, in such a way that the first longitudinal string 30a is inserted into the cylindrical stent body 14 through one corresponding mesh 12, extends a predetermined length through the interior of the stent body 14, and comes out of the stent body 14 through another mesh 12.

Furthermore, a circumferential string 40 integrally extends at a first end thereof from a second end of the first longitudinal string 30a and is woven with the cylindrical stent body 14 into a circular shape through corresponding mesh 12 which is arranged in the circumferential direction of the cylindrical stent body 14.

In addition, a second longitudinal string 30b extends at a first end thereof from a second end of the circumferential string 40 and is woven with the cylindrical stent body 14 through corresponding mesh 12 in a zigzag manner such that the second longitudinal string 30b crosses over the first longitudinal string 30a on the circumference of the string. A second end string 20b extends at a first end thereof from a second end of the second longitudinal string 30b such that the second end string 20b is symmetrical with the first end string 20a. A second end of the second end string 20b is tied to the first end of the first end string 201, thus forming a hook loop 20c.

Figure 22:
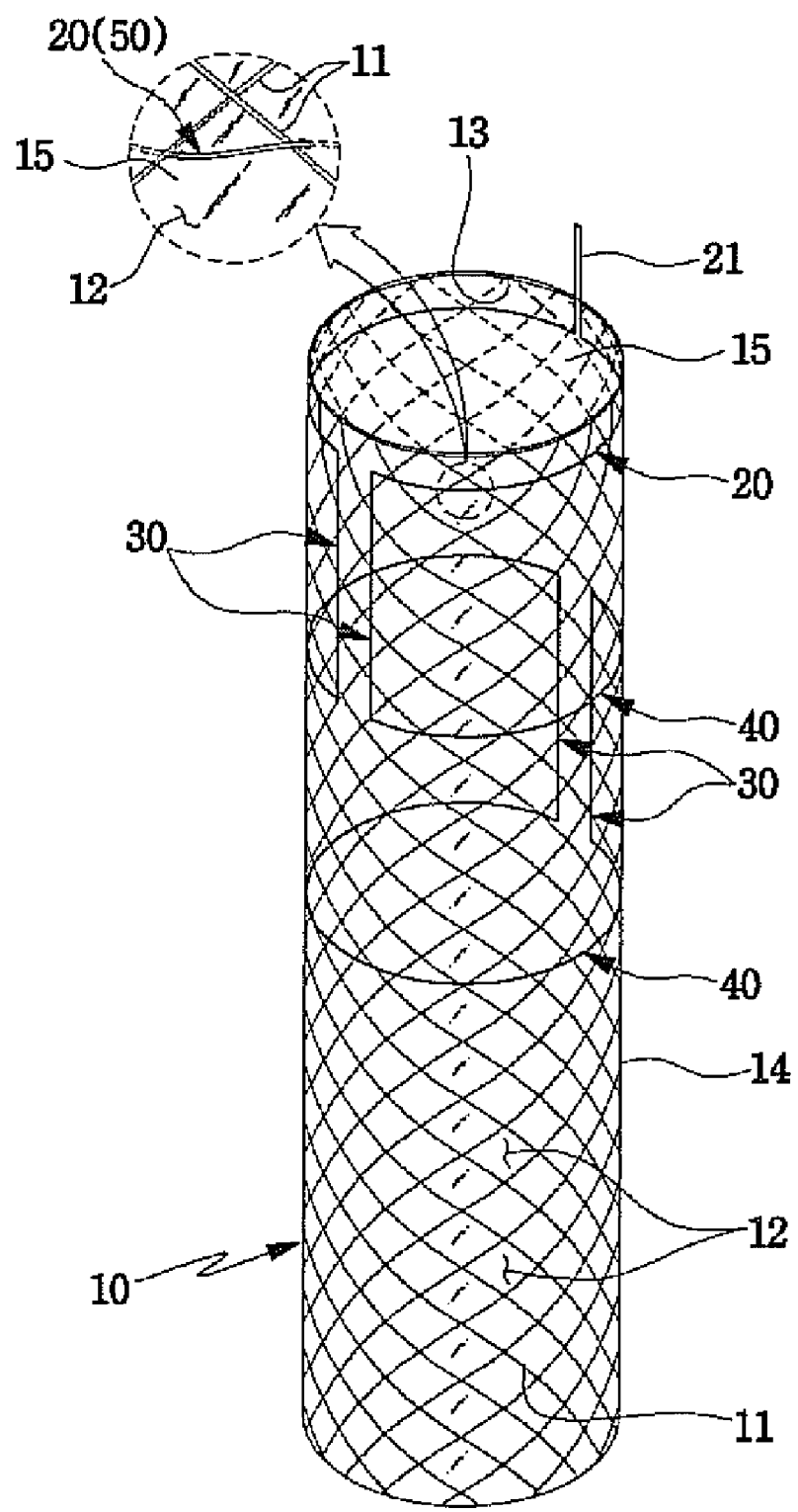
FIG. 22 is a perspective view showing the drawstring of FIG. 4 applied to a cylindrical stent having an inner surface to which a film is attached.
Figure 23:
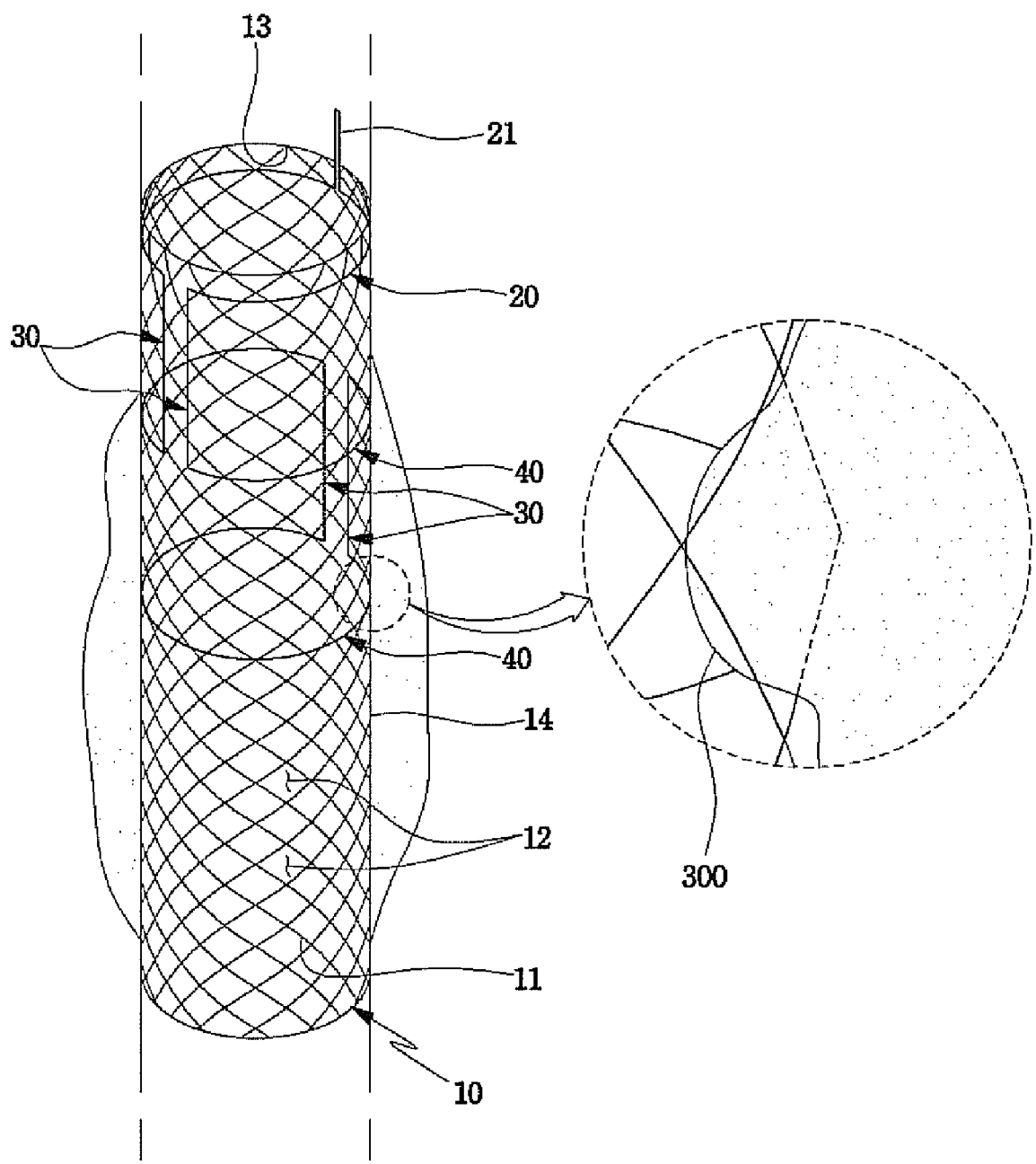
FIG. 23 is of a view showing placement of the stent having the drawstring of FIG. 4 on a lesion portion and an enlarged sectional view showing lumen tissue which has penetrated into a mesh of the stent.
Figure 24:
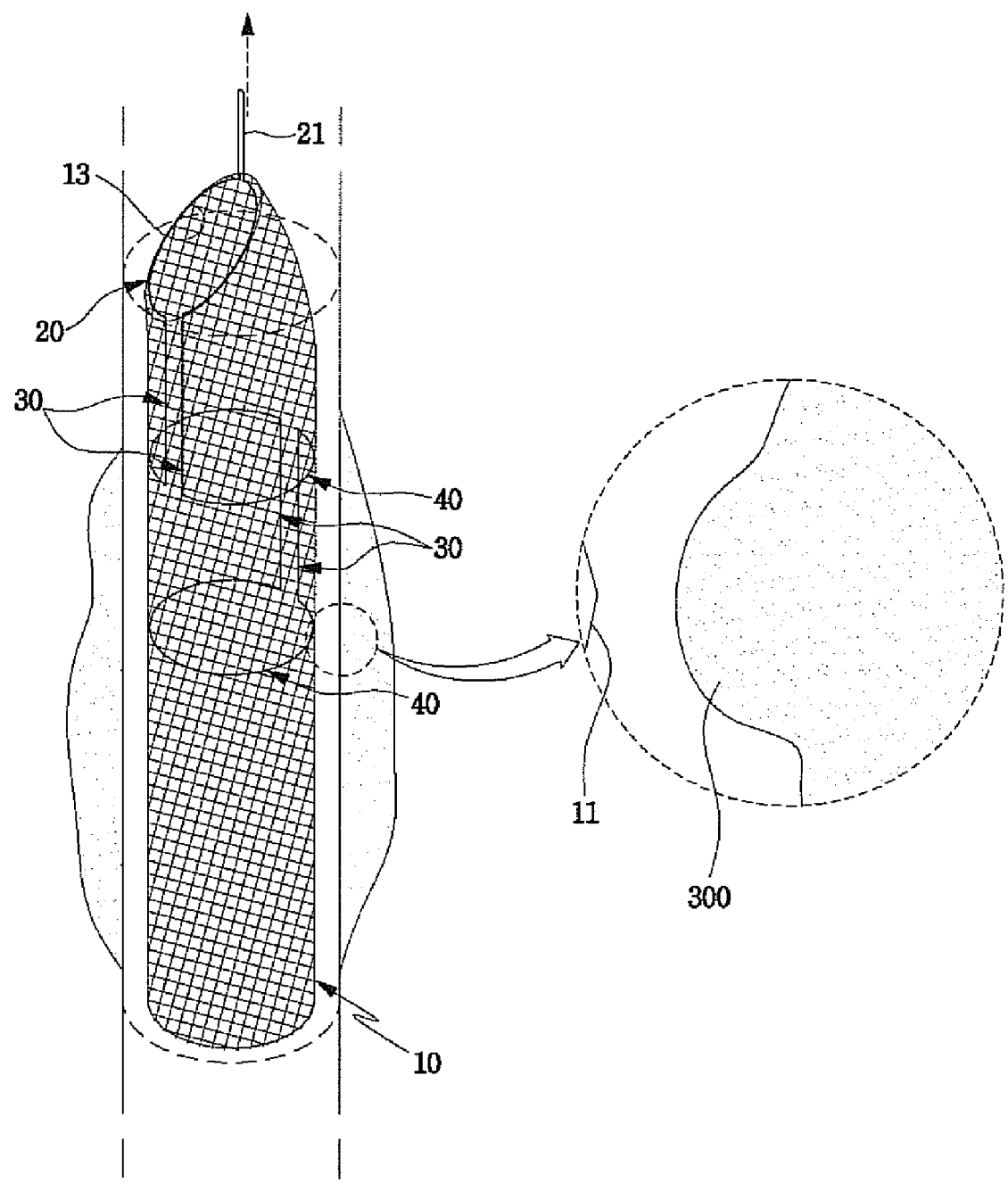
FIG. 24 is of a view illustrating the state of the stent when the drawstring is pulled to remove the stent from a body and an enlarged sectional view showing separation of the penetrated lumen tissue from the stent according to the present invention.

Hereinafter, the case where the embodiments of the drawstring of the present invention are applied to other types of stents will be explained. As shown in FIG. 22, in the stent 10 of this case, a cylindrical stent body 14 is formed by weaving one or more strands of shape memory alloy wires 11 or crossing them with each other in a zigzag manner such that mesh 12 is defined by the wires 11 and bent portions 13 are formed along the circumferences of both ends of the cylindrical stent body 14. In addition, a medical film 15 is attached to the inner wall of the cylindrical stent body 14.

The drawstring 50 has an end string 20 which is formed on one end of the cylindrical stent body 14 into an annular shape in such a way that it is threaded into corresponding mesh 12 and the film 15 of the cylindrical stent body 14 in a zigzag manner. A hook loop 21 is formed by tying both ends of the end string 20.

Furthermore, a longitudinal string 30 integrally extends from the end string 30 or a first end of the longitudinal string 30 is tied to the end string 30. The longitudinal string 30 is threaded through the film 15 and corresponding mesh 12 which is arranged with respect to the longitudinal direction of the cylindrical stent body 14, in such a way that the longitudinal string 30 is inserted into the cylindrical stent body 14 through the film 15 and one corresponding mesh 12, extends a predetermined length through the interior of the stent body 14, and comes out of the stent body 14 through the film 15 and another mesh 12.

In addition, at least one circumferential string 40 having an annular shape is formed in a predetermined portion of the cylindrical stent body 14 in such a way that it is threaded, in a zigzag manner, into the film 15 and into the mesh 12 which is disposed in the circumferential direction of the cylindrical stent body 14. The circumferential string 40 integrally extends from a second end of the longitudinal string 30 or is tied thereto. In the present invention, the stent 10 having the drawstring 50 can be configured in the above-mentioned manner.

In the stent 10, when the hook loop 21 is pulled, the end string 20, the longitudinal string 30 and the circumferential string 40 are pulled in consecutive order. Here, the end string 20 is pulled in the diametrical and longitudinal directions of the cylindrical stent body 14. The longitudinal string 30 is pulled in the longitudinal direction of the cylindrical stent body 14. The circumferential string 40 is pulled in the diametrical direction of the cylindrical stent body 14. As a result, the stent 10 can be easily separated from the inner surface of a lumen in the patients' body.

1. As shown in FIG. 4, the drawstring 50 according to the first embodiment of the present invention integrally includes a first end string 20a, a first longitudinal string 30a, a circumferential string 40, a second longitudinal string 30b and a second end string 20b.

The first end string 20a is woven with the cylindrical stent body 14 of the stent 10 to form a semicircular shape in such a way that it is threaded into corresponding mesh 12 of the cylindrical stent body 14 and the film 15 in a zigzag manner.

The first longitudinal string 30a extends at a first end thereof from a second end of the first end string 20a and passes through the film 15 and through corresponding mesh 12 which is arranged with respect to the longitudinal direction of the cylindrical stent body 14, in such a way that the first longitudinal string 30a is inserted into the cylindrical stent body 14 through one corresponding mesh 12 and the film 15, extends a predetermined length through the interior of the stent body 14, and comes out of the stent body 14 through another mesh 12 and the film 15.

The circumferential string 40 is integrally extended at a first end thereof from a second end of the first longitudinal string 30a and is woven through the film 15 and through corresponding mesh 12 which is arranged in the circumferential direction of the cylindrical stent body 14. The circumferential string 40 may comprise one or more circumferential strings 40 which have a semicircular shape and/or a circular shape.

At a first end of the second longitudinal string 30b, the second longitudinal string 30b integrally extends from a second end of the circumferential string 40 such that the second longitudinal string 30b is parallel to the first longitudinal string 30a. The second end string 20b integrally W extends at a first end thereof from a second end of the second longitudinal string 30b such that the second end string 20b is symmetrical with the first end string 20a. Thereafter, a hook loop 20c is formed by tying a second end of the second end string 20b to the first end of the first end string 20a.

As such, the drawstring 50 of the first embodiment is configured such that the first end string 20a, the first longitudinal string 30a, the circumferential string 40, the second longitudinal string 30b and the second end string 20b are integrally formed into a single string.

2. As shown in FIG. 5, the drawstring 50 according to the second embodiment of the present invention integrally includes a first end string 20a, a first longitudinal string 30a, a circumferential string 40, a second longitudinal string 30b and a second end string 20b.

The first end string 20a is woven with the cylindrical stent body 14 of the stent 10 to form a semicircular shape in such a way that it is threaded into the film 15 and into corresponding mesh 12 of the cylindrical stent body 14 in a zigzag manner.

The first longitudinal string 30a extends at a first end thereof from a second end of the first end string 20a and passes through the film 15 and through corresponding mesh 12 which is arranged with respect to the longitudinal direction of the cylindrical stent body 14, in such a way that the first longitudinal string 30a is inserted into the cylindrical stent body 14 through one corresponding mesh 12 and the film 15, extends a predetermined length through the interior of the stent body 14, and comes out of the stent body 14 through another mesh 12 and the film 15.

The circumferential string 40 integrally extends at a first end thereof from a second end of the first longitudinal string 30a and is woven through the film 15 and through corresponding mesh 12 which is arranged in the circumferential direction of the cylindrical stent body 14. The circumferential string 40 may comprise one or more circumferential strings 40 which have a circular shape.

The second longitudinal string 30b integrally extends at a first end thereof from a second end of the circumferential string 40 such that the second longitudinal string 30b and the first longitudinal string 30a cross over each other. The second end string 20b integrally extends at a first end thereof from a second end of the second longitudinal string 30b such that the second end string 20b is symmetrical with the first end string 20a. Thereafter, a hook loop 20c is formed by tying a second end of the second end string 20b to the first end of the first end string 20a.

3. As shown in FIG. 6, the drawstring 50 according to the third embodiment of the present invention integrally includes a first end string 20a, a first longitudinal string 30a, a circumferential string 40, a second longitudinal string 30b and a second end string 20b.

The first end string 20a is woven with the cylindrical stent body 14 of the stent 10 to form a semicircular shape in such a way that it is threaded into the film 15 and corresponding mesh 12 of the cylindrical stent body 14 in a zigzag manner.

The first longitudinal string 30a extends at a first end thereof from a second end of the first end string 20a and passes through the film 15 and corresponding mesh 12 which is arranged with respect to the diagonal direction of the cylindrical stent body 14, in such a way that the first longitudinal string 30a is inserted into the cylindrical stent body 14 through one corresponding mesh 12 and the film 15, extends a predetermined length through the interior of the stent body 14, and comes out of the stent body 14 through another mesh 12 and the film 15.

The circumferential string 40 integrally extends at a first end thereof from a second end of the first longitudinal string 30a and is woven through the film 15 and through corresponding mesh 12 which is arranged in the circumferential direction of the cylindrical stent body 14. The circumferential string 40 may comprise one or more circumferential strings 40 which have a circular shape.

The second longitudinal string 30b extends at a first end thereof from a second end of the circumferential string 40 and is woven through the film 15 and corresponding mesh 12 in a zigzag manner such that the second longitudinal string 30b crosses over the first longitudinal string 30a.

The second end string 20b extends at a first end thereof from a second end of the second longitudinal string 30b and is configured such that it faces and is spaced apart from the first end string 20a. Thereafter, a hook loop 20c is formed by tying a second end of the second end string 20b to the first end of the first end string 20a.

As such, the drawstring 50 of the third embodiment is configured such that the first end string 20a, the first longitudinal string 30a, the circumferential string 40, the second longitudinal string 30b and the second end string 20b are integrally formed into a single string.

4. As shown in FIG. 7, in the drawstring 50 according to the fourth embodiment of the present invention, an end string 20 is woven with the cylindrical stent body 14 of the stent 10 to form a circular shape in such a way that it is threaded into the film 15 and corresponding mesh 12 of the cylindrical stent body 14 in a zigzag manner. A hook loop 21 is formed by tying both ends of the end string 20 to each other.

One or more longitudinal strings 30 are tied at first ends thereof to the hook loop 21 of the end string 20. Each longitudinal string 30 passes through the film 15 and through corresponding mesh 12 which is arranged with respect to the longitudinal direction of the cylindrical stent body 14, in such a way that the longitudinal string 30 is inserted into the cylindrical stent body 14 through one corresponding mesh 12 and the film 15, extends a predetermined length through the interior of the stent body 14, and comes out of the stent body 14 through another mesh 12 and the film 15.

Furthermore, one or more circumferential strings 40 are woven with the cylindrical stent body 14 into circular shapes through the film 15 and through corresponding mesh 12 which is arranged in the circumferential direction of the cylindrical stent body 14. Each circumferential string 40 is tied to a second end of the corresponding longitudinal string 30.

5. As shown in FIG. 8, in the drawstring 50 according to the fifth embodiment of the present invention, an end string 20 is woven with the cylindrical stent body 14 of the stent 10 to form a circular shape in such a way that it is threaded into the film 15 and corresponding mesh 12 of the cylindrical stent body 14 in a zigzag manner. A hook loop 21 is formed by tying both ends of the end string 20 to each other.

Furthermore, one or more circumferential strings 40 are woven with the cylindrical stent body 14 into circular shapes through the film 15 and through corresponding mesh 12 which is arranged in the circumferential direction of the cylindrical stent body 14. Both ends of each circumferential string 40 are tied to each other to form a tie loop 41. The tie loops 41 of the circumferential strings 40 are tied to the hook loop 21 of the end string 20.

6. As shown in FIG. 9, in the drawstring 50 according to a sixth embodiment of the present invention, a first end string 20a is woven with the cylindrical stent body 14 of the stent 10 to form a semicircular shape in such a way that the first end string 20a is threaded into the film 15 and corresponding mesh 12 of the cylindrical stent body 14 in a zigzag manner.

The first longitudinal string 30a extends at a first end thereof from a second end of the first end string 20a and passes through the film 15 and corresponding mesh 12 which is arranged with respect to the longitudinal direction of the cylindrical stent body 14, in such a way that the first longitudinal string 30a is inserted into the cylindrical stent body 14 through one corresponding mesh 12 and the film 15, extends a predetermined length through the interior of the stent body 14, and comes out of the stent body 14 through another mesh 12 and the film 15.

Furthermore, a circumferential string 40 integrally extends at a first end thereof from a second end of the first longitudinal string 30a and is woven with the cylindrical stent body 14 into a circular shape through the film 15 and corresponding mesh 12 which is arranged in the circumferential direction of the cylindrical stent body 14.

In addition, a second longitudinal string 30b extends at a first end thereof from a second end of the circumferential string 40 and is woven with the cylindrical stent body 14 through the film 15 and corresponding mesh 12 in a zigzag manner such that the second longitudinal string 30b crosses over the first longitudinal string 30a on the circumference of the string. A second end string 20b extends at a first end thereof from a second end of the second longitudinal string 30b such that the second end string 20b is symmetrical with the first end string 20a. A second end of the second and string 20b is tied to the first end of the first end string 201, thus forming a hook loop 20c.

In the case where two or more circumferential strings 40 are provided, a distance between adjacent circumferential strings 40 can be adjusted depending on an area of a lesion or the entire length of the stent 10.

Furthermore, the length of the longitudinal string 30 is determined depending on an area of a lesion or the entire length of the stent 10.

Each of the first and second longitudinal strings 30a and 30b is woven with the cylindrical stent body 14 of the stent in such a way that it is threaded in a zigzag manner through the film 15 and the corresponding mesh 12 which is arranged in the longitudinal direction of the cylindrical stent body 14.

In addition, the longitudinal string 30 may be configured such that it is threaded in a zigzag manner into corresponding mesh 12 which is arranged in the longitudinal direction of the cylindrical stent body 14.

The drawstring 50 is made of one selected from the group including a medical fiber, synthetic resin, nonferrous metal and a metal wire.

The drawstring 50 of the present invention can be applied to a cylindrical stent, a stent which is extended in diameter on both ends thereof, or a stent which is reduced in diameter on both ends thereof.

The operation and effect of the present invention having the above-mentioned structure will be explained below.

When a lesion occurs on a lumen in a human body and the diameter of a portion of the lumen that has the lesion is thus contracted by extension of the lesion, a stent insertion operation is given to widen the diameter of the portion having the lesion.

With regard to the stent insertion operation, the target portion of the lumen having the lesion is determined. Thereafter, a stent 10 is inserted into the target portion of the lumen with the lesion by a stenting device (not shown) so as to expand the contracted target portion where the lesion is.

The stent 10 which is placed in the target portion remains there until the lesion is removed and the target portion of the lumen has completely recovered. Typically, a duration for which the stent 10 remains in the lumen is about six months. The duration may vary depending on characteristics of the lesion or the progress after the stent insertion operation.

Here, if the stent 10 is placed on the lesion portion 300 for a long period of time, tissues of the lesion portion 300 penetrate into the mesh 12 of the stent 10. In the present invention, even if tissues of the lesion penetrate into the stent 10, the stent 10 can be easily separated from the lesion portion 300 or other lumen tissues by the drawstring 50.

When an operation of removing the stent 10 is conducted after the lesion portion 300 is removed or when the stent 10 is removed to conduct a restenting operation, a stent removal device is used.

Hereinafter, the operation of the drawstrings 50 according to the six embodiments when the stents 10 are removed will be explained. The first, second and third embodiments will be separately explained.

Figure 10:
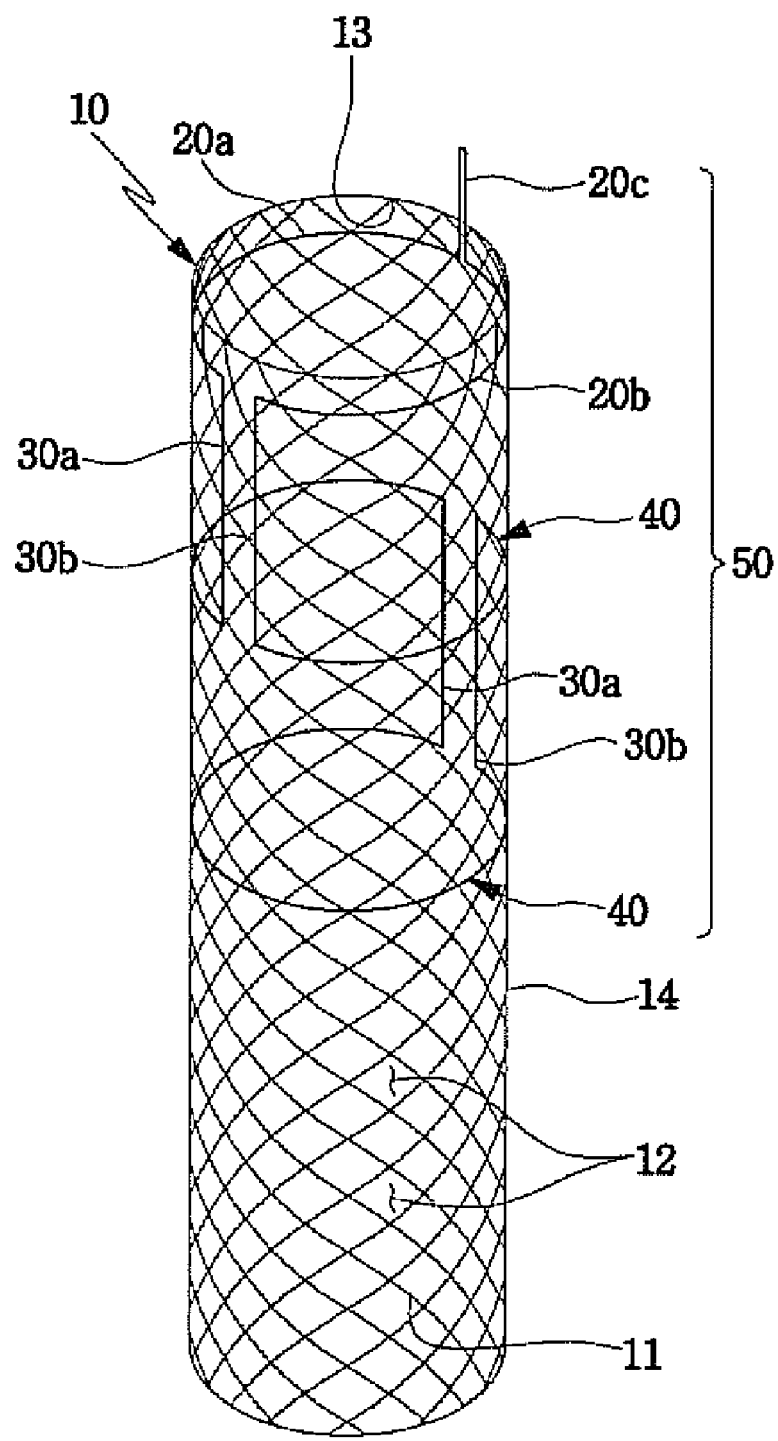
FIG. 10 is a perspective view showing the drawstring of FIG. 4 applied to a cylindrical stent.
Figure 16:
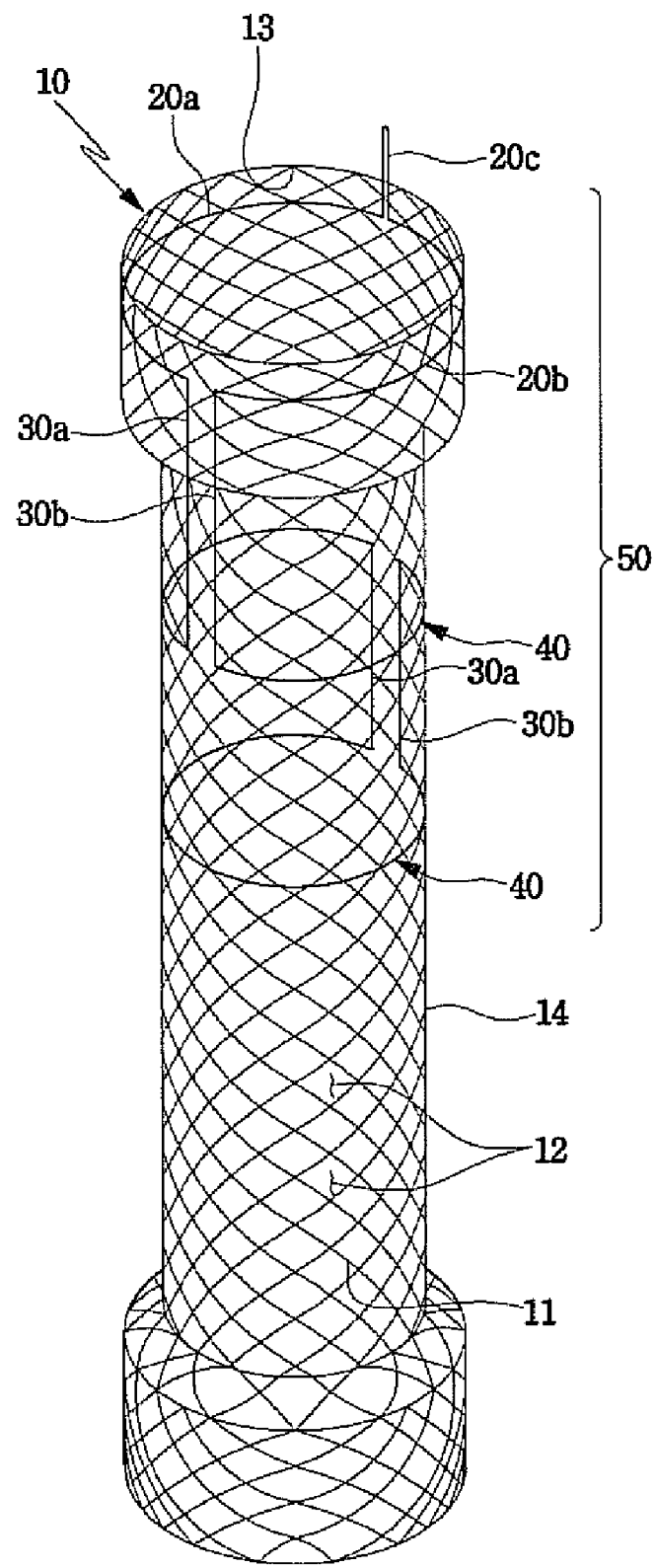
FIG. 16 is a perspective view showing the drawstring of FIG. 4 applied to a stent both ends of which have become wider in diameter.

First, as shown in FIGS. 4, 10 and 16, in the drawstring 50 according to the first embodiment, when the drawstring 50 is pulled in the direction in which it is extracted, the pulling force is transmitted to the drawstring 50 in a sequence of the hook loop 20c→the first and second end strings 20a and 20b→the first and second longitudinal strings 30a and 30b→the circumferential string 40. Thereby, the stent 10 is reduced in diameter and simultaneously extended in length.

Here, when the first and second end strings 20a and 20b are pulled by the pulling force, they are reduced in diameter and thus compress the cylindrical stent body 14 towards the diametrical center of the cylindrical stent body 14.

Furthermore, the first and second longitudinal strings 30a and 30b are pulled in the longitudinal direction of the stent 10 by the pulling force transmitted from the first and second end strings 20a and 20b.

In addition, the circumferential string 40 is contracted by the pulling force transmitted from the first and second end strings 20a and 20b and the first and second longitudinal strings 30a and 30b, thus compressing the cylindrical stent body 14 such that it is reduced in diameter.

Therefore, even when the stent 10 is in a state of being grasped by lumen tissue, the stent 10 is extended in the longitudinal direction by the first and second end strings 20a and 20b and the first and second longitudinal strings 30a and 30b and simultaneously contracted in diameter towards the central axis of the stent by the circumferential string 40. Thus, the stent 10 which has been grasped by the lumen tissue can be easily separated and removed from the lumen tissue, thereby preventing pain or secondary injury from being caused.

Figure 11:
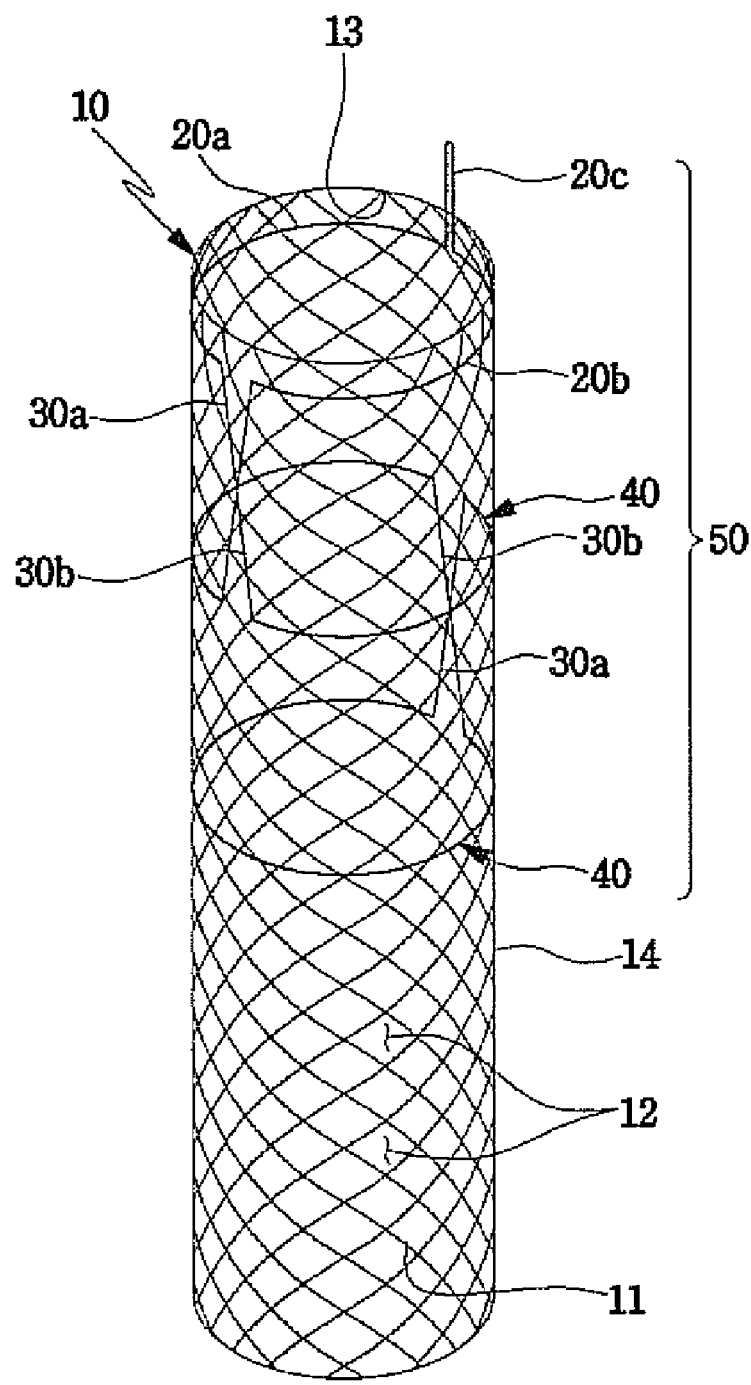
FIG. 11 is a perspective view showing the drawstring of FIG. 5 applied to a cylindrical stent.
Figure 17:
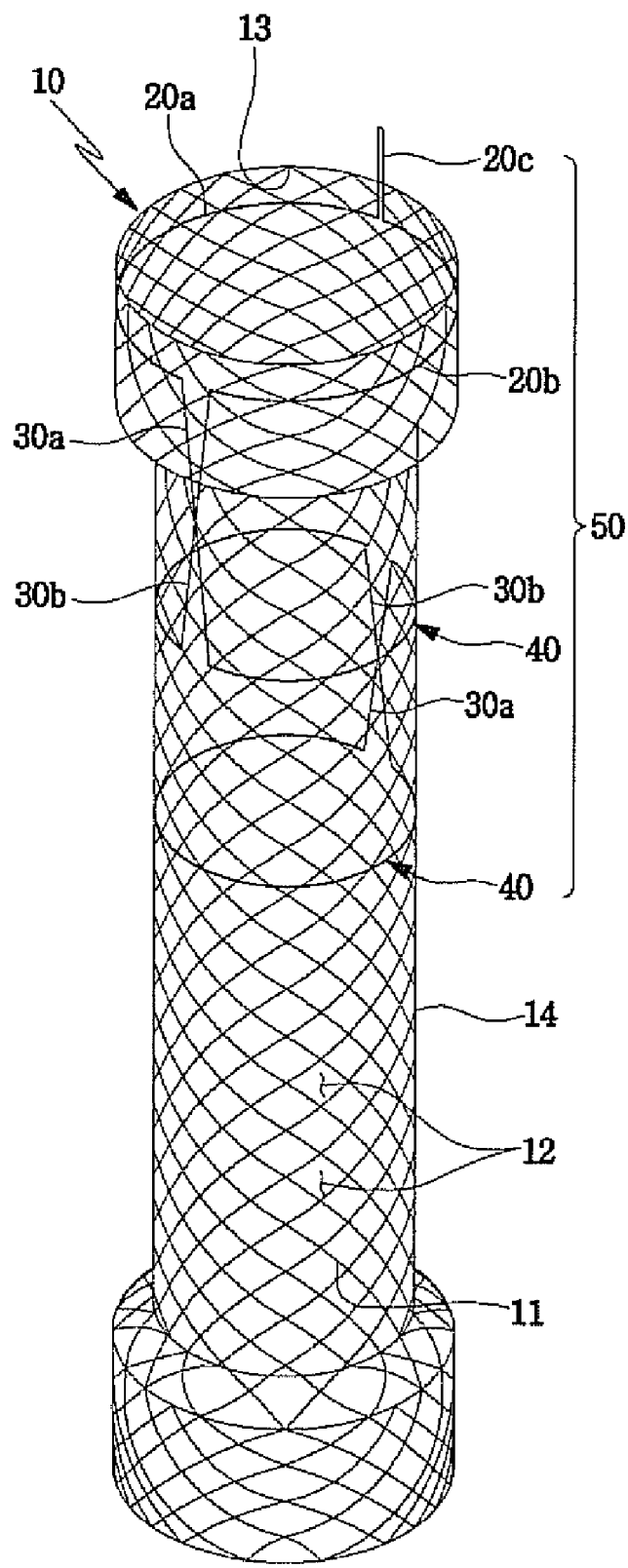
FIG. 17 is a perspective view showing the drawstring of FIG. 5 applied to a stent both ends of which have become wider in diameter.

Secondly, as shown in FIGS. 5, 11 and 17, in the drawstring 50 according to the second embodiment, when the drawstring 50 is pulled in the direction in which it is extracted, the pulling force is transmitted to the drawstring 50 in a sequence of the hook loop 20c→the first and second end strings 20a and 20b→the first and second longitudinal strings 30a and 30b→the circumferential string 40. Thereby, the stent 10 is reduced in diameter and simultaneously extended in length.

Here, when the first and second end strings 20a and 20b are pulled by the pulling force, their diameter is reduced and thus the cylindrical stent body 14 is compressed towards the diametrical center of the cylindrical stent body 14.

Furthermore, the first and second longitudinal strings 30a and 30b are pulled in the longitudinal direction of the stent 10 by the pulling force transmitted from the first and second end strings 20a and 20b, while the first and second longitudinal strings 30a and 30b maintain the state of intersection with each other.

In addition, the circumferential string 40 is contracted by the pulling force transmitted from the first and second end strings 20a and 20b and the first and second longitudinal strings 30a and 30b, thus compressing the cylindrical stent body 14 so that it is narrowed in diameter.

Therefore, even when the stent 10 is in a state of being grasped by lumen tissue, the stent 10 is extended in the longitudinal direction by the first and second end strings 20a and 20b and the first and second longitudinal strings 30a and 30b and simultaneously contracted in diameter towards the central axis of the stent 10 by the circumferential string 40.

Thus, the stent 10 which has been grasped by the lumen tissue can be easily separated and removed from the lumen tissue, thereby preventing pain or secondary injury from being caused.

Figure 12:
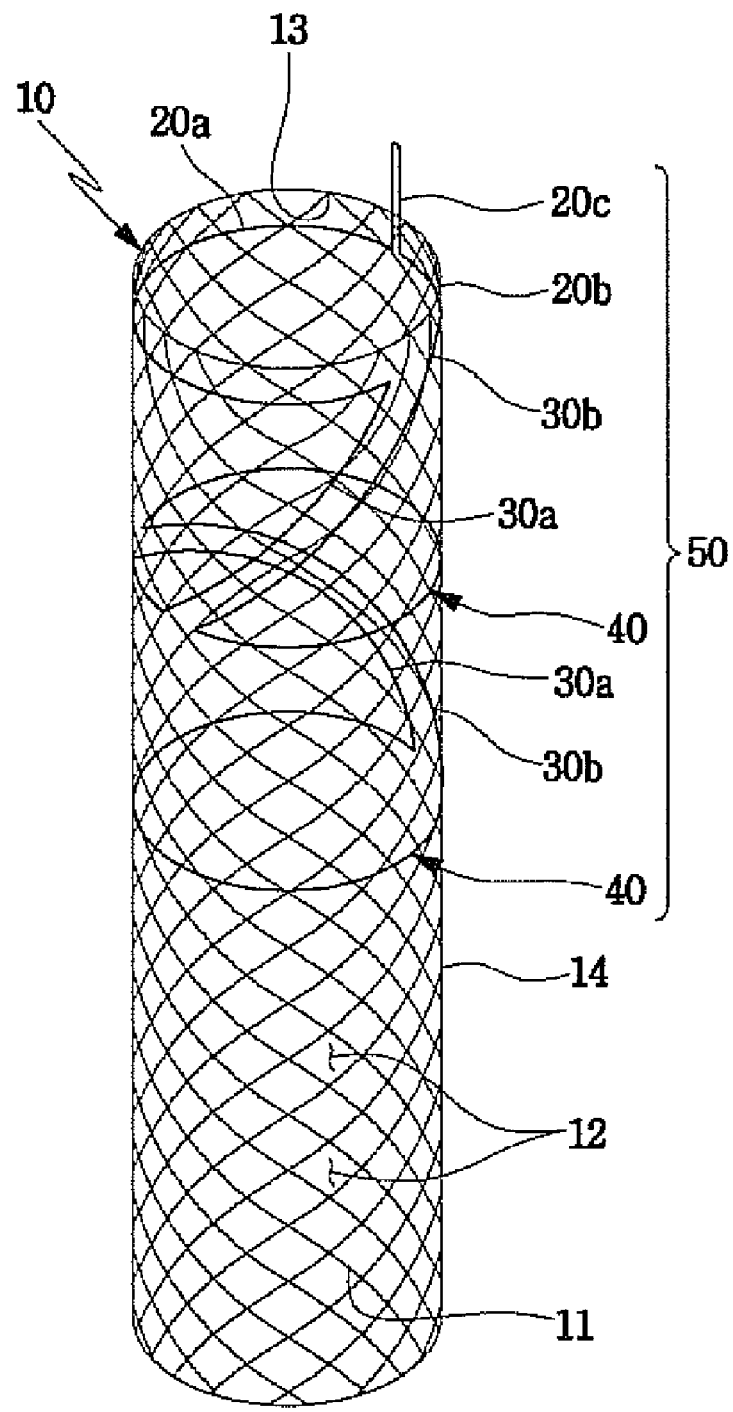
FIG. 12 is a perspective view showing the drawstring of FIG. 6 applied to a cylindrical stent.
Figure 18:
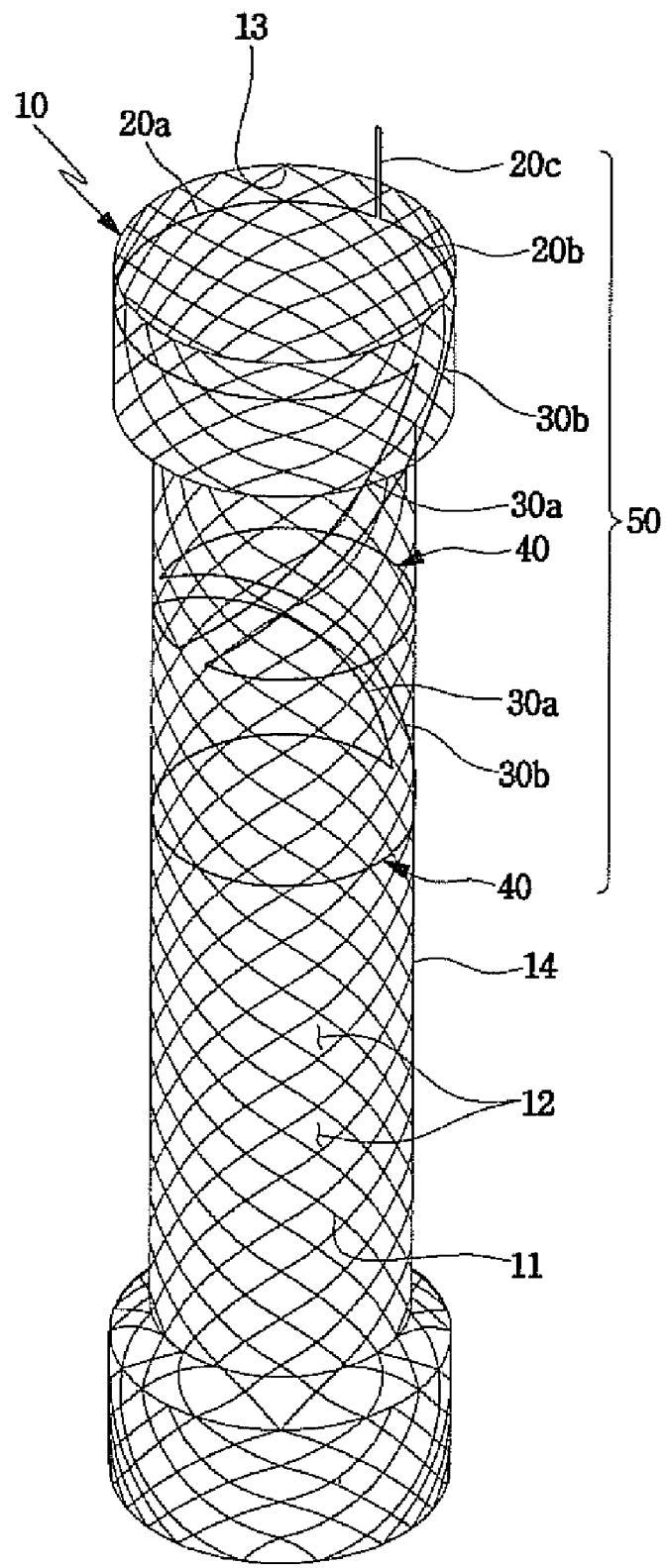
FIG. 18 is a perspective view showing the drawstring of FIG. 6 applied to a stent both ends of which have become wider in diameter.

Third, as shown in FIGS. 6, 12 and 18, in the drawstring 50 according to the third embodiment, when the drawstring 50 is pulled in the direction in which it is extracted, the pulling force is transmitted to the drawstring 50 in a sequence of the hook loop 20c→the first and second end strings 20a and 20b→the first and second longitudinal strings 30a and 30b→the circumferential string 40. Thereby, the diameter of the stent 10 is narrowed and the length is simultaneously extended.

Here, when the first and second end strings 20a and 20b are pulled by the pulling force, they are reduced in diameter and thus compress the cylindrical stent body 14 towards the diametrical center of the cylindrical stent body 14.

Furthermore, the first and second longitudinal strings 30a and 30b which are oriented in diagonal directions are pulled in the longitudinal direction and the circumferential direction of the stent 10 by the pulling force transmitted from the first and second end strings 20a and 20b.

In addition, the circumferential string 40 is contracted by the pulling force transmitted from the first and second end strings 20a and 20b and the first and second longitudinal strings 30a and 30b, thus compressing the cylindrical stent body 14 such that it is reduced in diameter.

Therefore, even when the stent 10 is in a state of being grasped by lumen tissue, the stent 10 is extended in the longitudinal direction by the first and second end strings 20a and 20b and the first and second longitudinal strings 30a and 30b and simultaneously contracted in diameter towards the central axis of the stent 10 by the circumferential string 40. Thus, the stent 10 which has been grasped by the lumen tissue can be easily separated and removed from the lumen tissue, thereby preventing pain or secondary injury from being caused.

Figure 13:
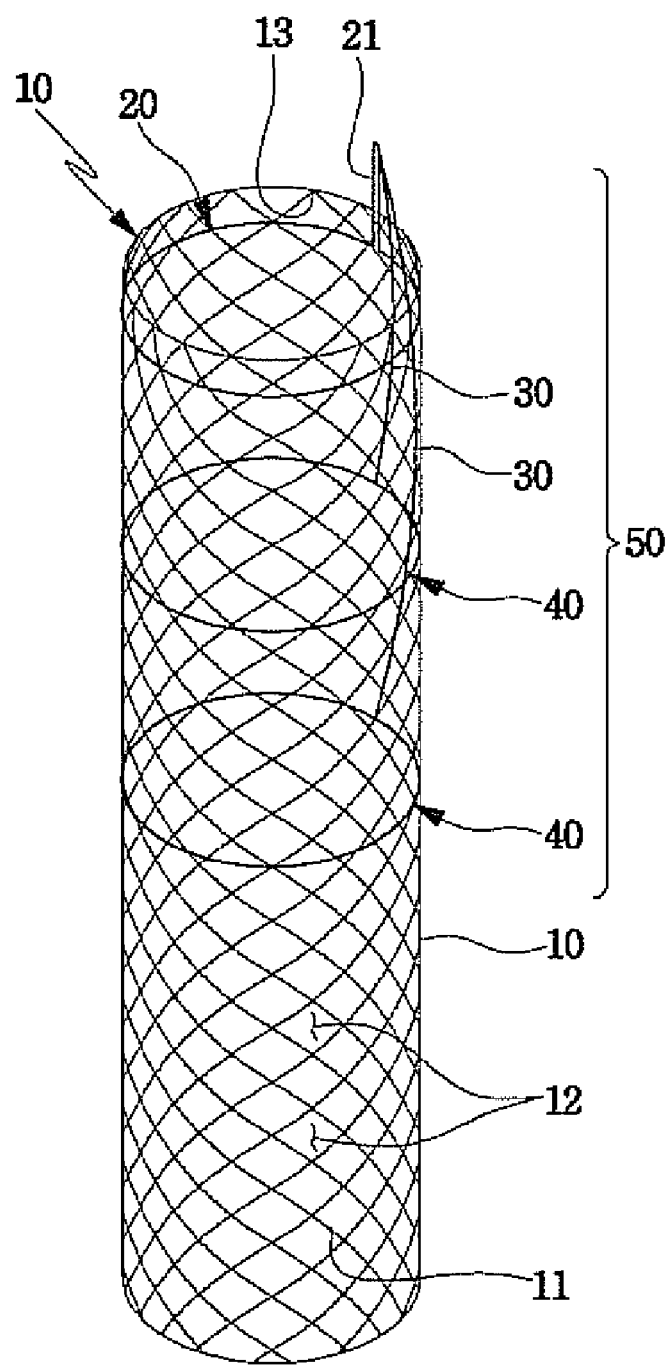
FIG. 13 is a perspective view showing the drawstring of FIG. 7 applied to a cylindrical stent.
Figure 19:
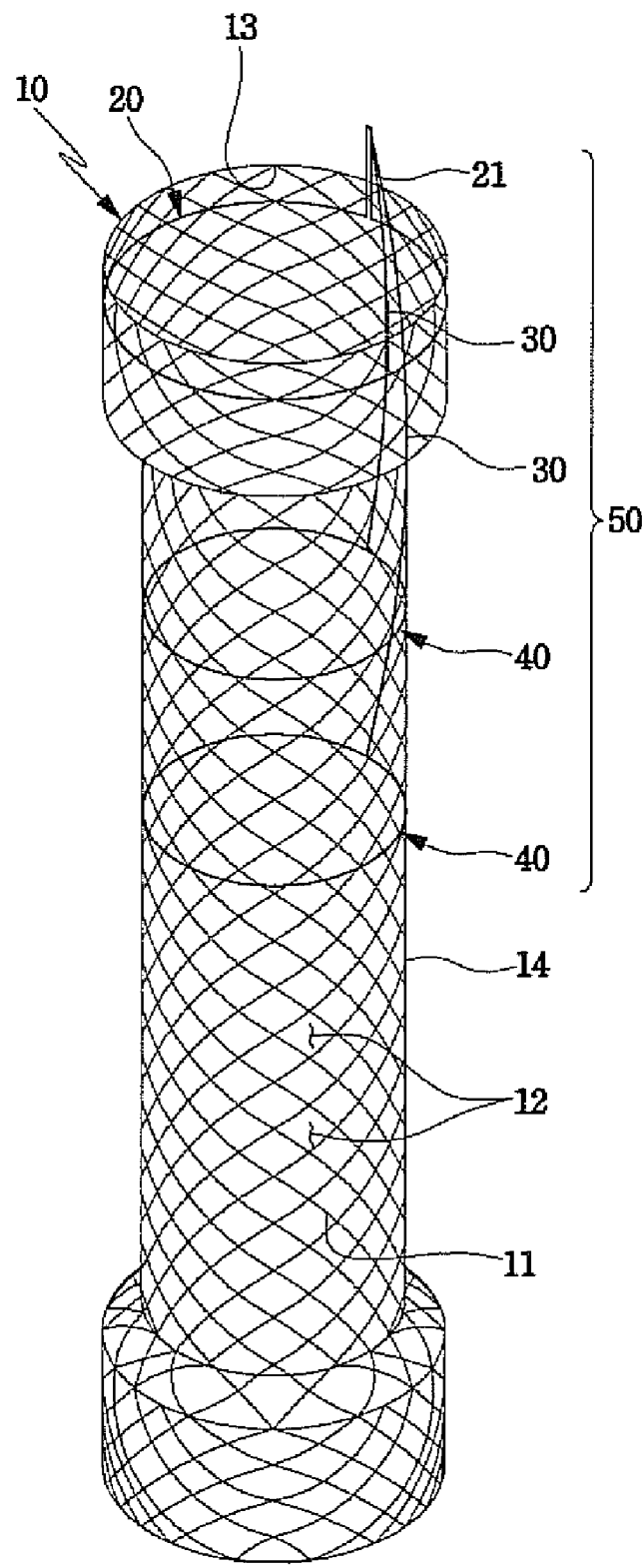
FIG. 19 is a perspective view showing the drawstring of FIG. 7 applied to a stent both ends of which have become wider in diameter.

Fourth, as shown in FIGS. 7, 13 and 19, in the drawstring 50 according to the fourth embodiment, when the drawstring 50 is pulled in the direction in which it is to be extracted, the pulling force is transmitted to the drawstring 50 in a sequence of the hook loop 21 and the longitudinal strings 30→the end string 20 and the circumferential strings 40. Thereby, the stent 10 is reduced in diameter and simultaneously extended in length.

Here, when the end string 20 is pulled by the pulling force, the annular end string 20 is narrowed in diameter and thus the cylindrical stent body 14 is compressed towards the diametrical center of the cylindrical stent body 14.

Furthermore, the longitudinal strings 30 are pulled in the longitudinal direction of the stent 10 and in a direction towards the central axis of the stent 10 at the same time by the pulling force transmitted from the hook loop 21.

In addition, the circumferential strings 40 are contracted by the pulling force transmitted from the corresponding longitudinal strings 30, thus compressing the cylindrical stent body 14 such that it is reduced in diameter.

Figure 14:
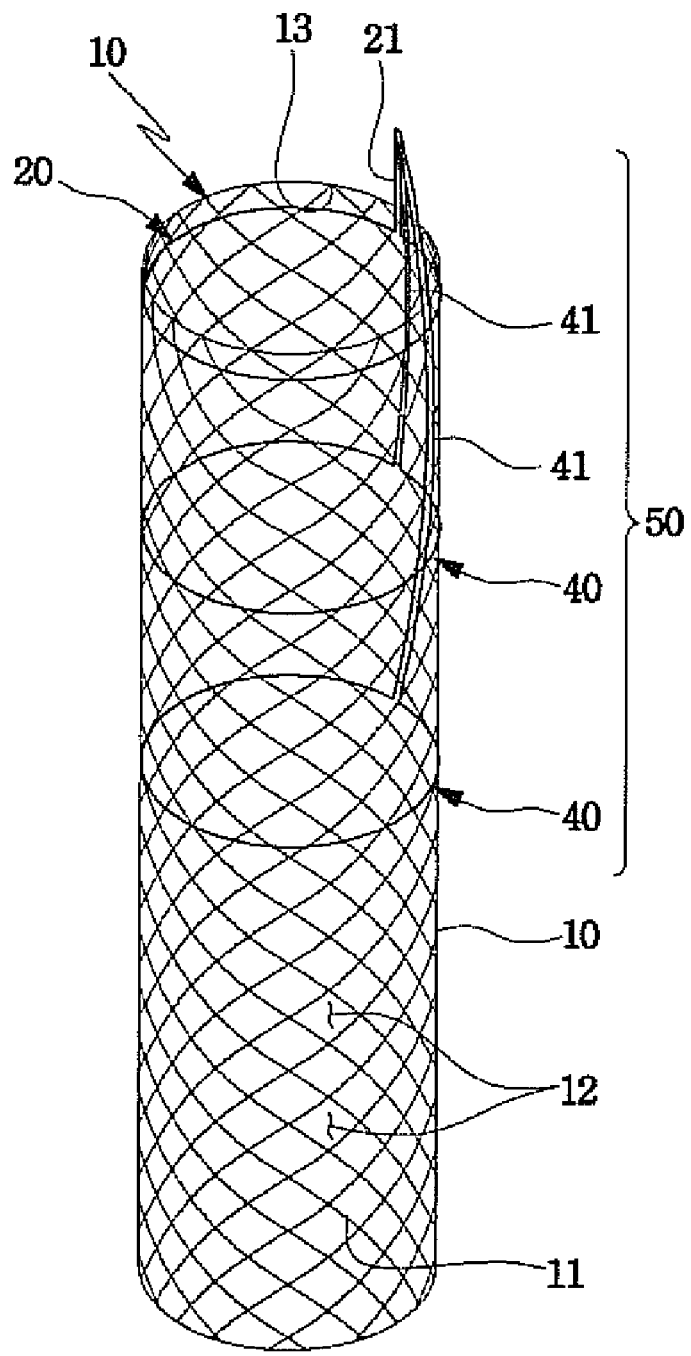
FIG. 14 is a perspective view showing the drawstring of FIG. 8 applied to a cylindrical stent.
Figure 20:
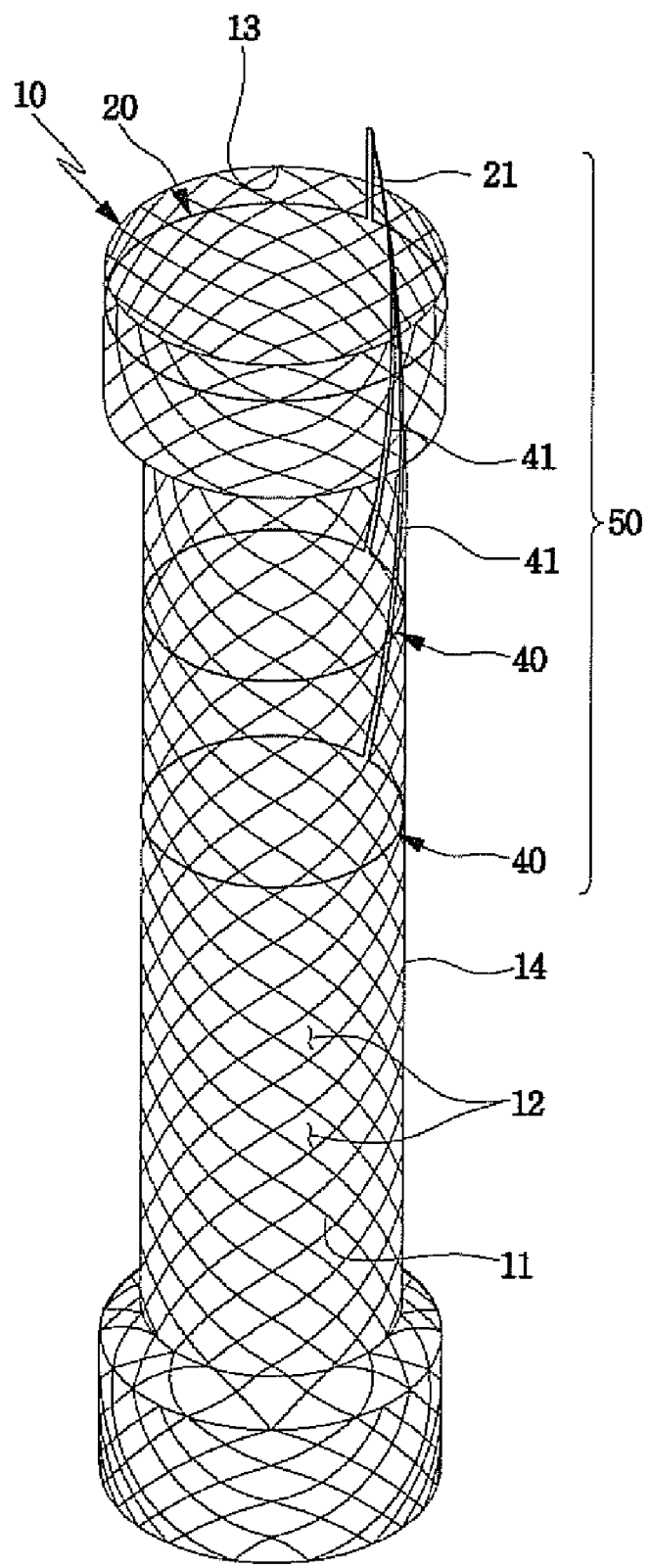
FIG. 20 is a perspective view showing the drawstring of FIG. 8 applied to a stent both ends of which have become wider in diameter.

Fifth, as shown in FIGS. 8, 14 and 20, in the drawstring 50 according to the fifth embodiment, when the drawstring 50 is pulled in the direction in which it is extracted, the pulling force is transmitted to the drawstring 50 in a sequence of the hook loop 21 and the tie loops 41 of the circumferential strings 40→the end string 20 and the circumferential strings 40. Thereby, the stent 10 is reduced in diameter and simultaneously extended in length.

Here, when the end string 20 is pulled by the pulling force, the annular end string 20 is narrowed in diameter and thus the cylindrical stent body 14 is compressed towards the diametrical center of the cylindrical stent body 14.

Furthermore, the tie loops 41 are pulled in the longitudinal direction of the stent 10 and in a direction towards the central axis of the stent 10 at the same time by the pulling force transmitted from the hook loop 21.

In addition, the circumferential strings 40 are contracted by the pulling force transmitted from the corresponding tie loops 41, thus compressing the cylindrical stent body 14 such that it is reduced in diameter.

Figure 15:
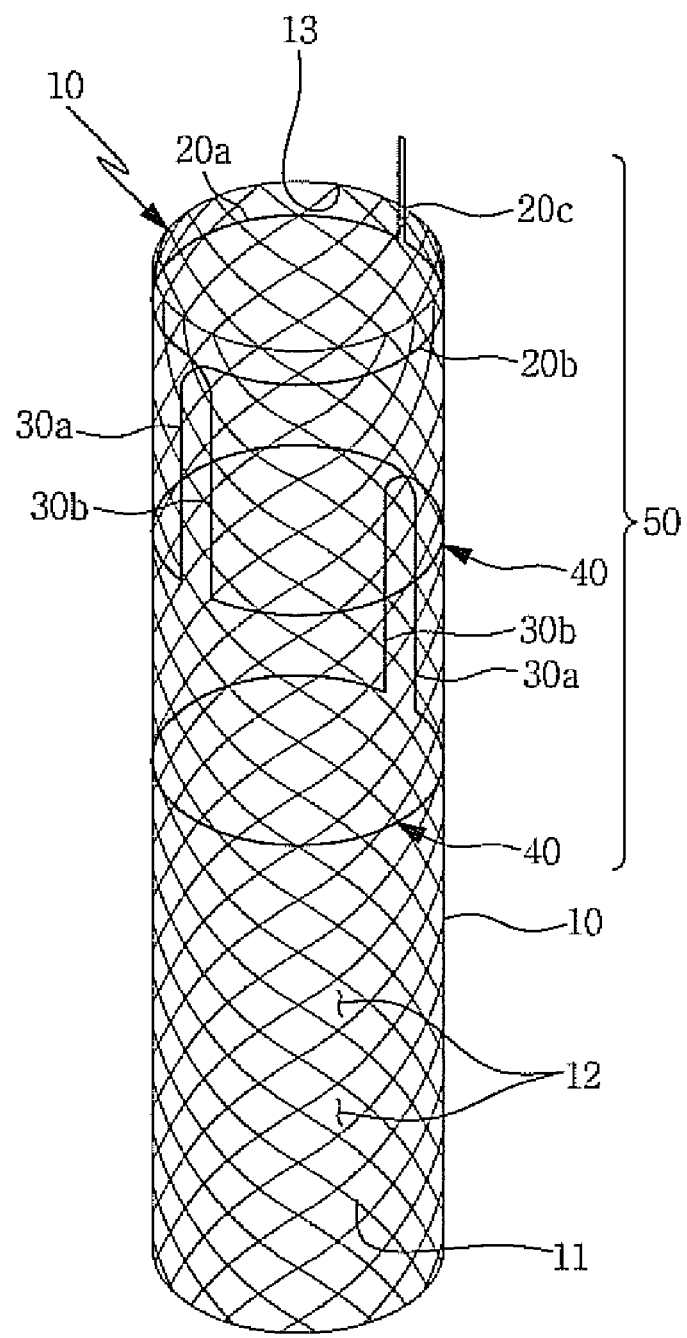
FIG. 15 is a perspective view showing the drawstring of FIG. 9 applied to a cylindrical stent.
Figure 21:
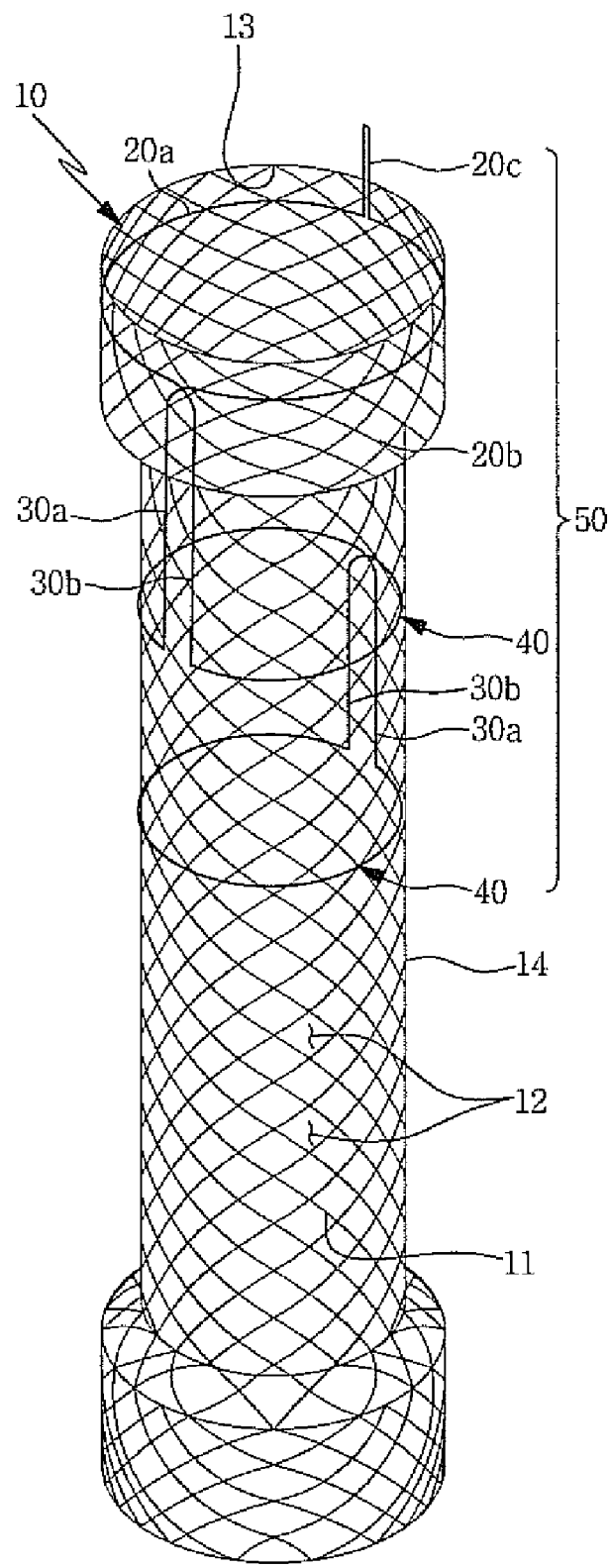
FIG. 21 is a perspective view showing the drawstring of FIG. 9 applied to a stent both ends of which have become wider in diameter.

Sixth, as shown in FIGS. 9, 15 and 21, in the drawstring 50 according to the sixth embodiment, when the drawstring 50 is pulled in the direction in which it is extracted, the pulling force is transmitted to the drawstring 50 in a sequence of the hook loop 20c→the first and second end strings 20a and 20b→the first and second longitudinal strings 30a and 30b→the circumferential string 40. Thereby, the stent 10 is reduced in diameter and simultaneously extended in length.

Here, when the first and second end strings 20a and 20b are pulled by the pulling force, the first and second end strings 20a and 20b which form the annular shape are narrowed and thus compress the cylindrical stent body 14 towards the diametrical center of the cylindrical stent body 14.

Furthermore, the first and second longitudinal strings 30a and 30b which cross over each other are pulled in the longitudinal direction and the circumferential direction of the stent 10 by the pulling force transmitted from the first and second end strings 20a and 20b.

In addition, the circumferential string 40 is contracted by the pulling force transmitted from the first and second end strings 20a and 20b and the first and second longitudinal strings 30a and 30b, thus compressing the cylindrical stent body 14 such that it is reduced in diameter.

In the embodiment, the first and second longitudinal strings 30a and 30b which face each other cross over each other on the circumference of the cylindrical stent body 14, so that the first and second longitudinal strings 30a and 30b are pulled by the pulling force in the longitudinal direction and the circumferential direction at the same time.

In the present invention, even when the stent 10 which has been deployed in a lumen having a lesion portion 300 is in a state of being grasped by the lesion portion 300 or lumen tissue which enters the mesh 12, the stent 10 can be easily separated and removed from the lumen, thereby preventing secondary injury from being caused, and preventing the patient from suffering pain.

Moreover, when the drawstring 50 is pulled, the stent 10 is extended in the longitudinal direction and reduced in diameter towards the diametrical center, so that the stent 10 can be easily separated from the lesion portion 300 or lumen tissue, thus facilitating the removal of the stent 10.

Furthermore, in the case where an area of the lesion portion 300 is relatively large, it is preferable that the distance between the circumferential strings 40 or the length of each longitudinal string 30 be reduced such that the force of separating the stent from the lesion portion 300 can be concentrated to facilitate the removal of the stent 10.

As described above, in a drawstring of the present invention, even if a stent is grasped by the inner wall of a lumen because the lumen tissue penetrates into the mesh of the stent, the stent can be easily separated from the lumen tissue in such a way as to reduce the diameter thereof without inflicting pain on a patient.

Furthermore, the drawstring is configured such that longitudinal strings and circumferential strings are provided in the stent. Thus, when an end string is pulled by a stent removal device to remove the stent from the lumen, the stent is extended in the longitudinal direction and simultaneously contracted in diameter such that it can be easily removed from the inner surface of the lumen. Thereby, secondary injury owing to the grasped stent is prevented, and pain of the patient can be reduced.

In addition, the drawstring can be configured in various shapes depending on the shape or characteristics of the stent to increase compatibility, thus facilitating the manufacture of the stent with the drawstring.

Moreover, the length of each longitudinal string or a distance between the circumferential strings can be adjusted depending on an area of a lesion portion in a lumen or the length of the stent, such that when the drawstring is pulled to remove the stent, a ratio of contraction of the stent is relatively uniform over the entire length of the stent. Thereby, depending on a degree with which the stent is grasped by the lumen tissue, the appropriate pulling force can be applied to the stent.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A stent system, comprising:
   a stent a cylindrical stent body formed by weaving at least one strand of a shape memory alloy wire such that mesh is defined by the wire and bent portions are formed along circumferences of opposite ends of the stent body; and
   a drawstring, comprising:
      an end string coupled in an end of the stent body in an annular shape in such a way that the end string passes, in a zigzag manner, through mesh arranged in a circumferential direction of the stent body, with a hook loop formed by tying opposite ends of the end string to each other, wherein the end string comprises first end string and a second end string, each of the first and second end strings having a semicircular shape, with the hook loop being formed by tying first ends of the first and second end strings to each other;
      a longitudinal string extending at a first end thereof from the end string, the longitudinal string being inserted into the stent body through mesh, and extending a predetermined length through an interior of the stent body, and coming out of the stent body through another mesh, wherein the longitudinal string comprises a first longitudinal string and a second longitudinal string which extend at first ends thereof from respective second ends of the first and second end strings; and
      a circumferential string extending from a second end of the longitudinal string, the circumferential string being formed in an annular shape in such a way that the circumferential string passes, in a zigzag manner, through mesh arranged in the circumferential direction of the stent body, wherein the circumferential string extends between second ends of the first and second longitudinal strings,
   whereby, when the hook loop is pulled, the end string, the longitudinal string and the circumferential string are consecutively pulled in such a way that the end string is pulled in diametrical and longitudinal directions of the stent body, the longitudinal string is pulled in the longitudinal direction of the stent body, and the circumferential string is pulled in the diametrical direction of the stent body.

2. The stent system, as set forth in claim 1, wherein a length of the longitudinal string is determined depending on an area of a lesion portion or a length of the stent.

3. The stent system, as set forth in claim 1, wherein lengths of the first and second longitudinal strings are determined depending on an area of a lesion portion or a length of the stent.

4. The stent system, as set forth in claim 1, wherein the longitudinal string passes, in a zigzag manner, through mesh arranged in the longitudinal direction of the stent body.

5. The stent system, as set forth in claim 1, wherein the first and second longitudinal strings pass, in a zigzag manner, through mesh arranged in the longitudinal direction of the stent body.

6. The stent system, as set forth in claim 1, wherein the drawstring is made of one of a medical fiber, a synthetic resin, a nonferrous metal, or a metal wire.

7. The stent system, as set forth in claim 1, further comprising:
   at least one additional circumferential string; and
   an additional longitudinal string connecting the circumferential strings to each other,
   wherein a distance between the circumferential strings is determined depending on an area of a lesion portion or a length of the stent.

8. A stent system, comprising:
   a stent having a cylindrical stent body formed by weaving at least one strand of a shape memory alloy wire such that mesh is defined by the wire and bent portions are formed along circumferences of opposite ends of the stent body, with a medical film applied to an inner wall of the stent body; and
   a drawstring comprising:
      an end string coupled in an end of the stent body in an annular shape in such a way that the end string passes, in a zigzag manner, through the film and through mesh arranged in a circumferential direction of the stent body, with a hook loop formed by tying opposite ends of the end string to each other, wherein the end string comprises a first end string and a second end string, each of the first and second end strings having a semicircular shape, with the hook loop being formed by tying first ends of the first and second end strings to each other;
      a longitudinal string extending at a first end thereof from the end string, the longitudinal string being inserted into the stent body through the film and mesh, and extending a predetermined length through an interior of the stent body, and coming out of the stent body through the film and another mesh, wherein the longitudinal string comprises a first longitudinal string and a second longitudinal string which extend at first ends thereof from respective second ends of the first and second end strings; and
      a circumferential string extending from a second end of the longitudinal string, the circumferential string being formed in an annular shape in such a way that the circumferential string passes, in a zigzag manner, through the film and through mesh arranged in the circumferential direction of the stent body, wherein the circumferential string extends between second ends of the first and second longitudinal strings,
   whereby, when the hook loop is pulled, the end string, the longitudinal string and the circumferential string are consecutively pulled in such a way that the end string is pulled in diametrical and longitudinal directions of the stent body, the longitudinal string is pulled in the longitudinal direction of the stent body, and the circumferential string is pulled in the diametrical direction of the stent body.

9. The stent system, as set forth in claim 8, further comprising:

at least one additional circumferential string; and an additional longitudinal string connecting the circumferential strings to each other, wherein a distance between the circumferential strings is determined depending on an area of a lesion portion or a length of the stent.

10. The stent system, as set forth in claim 8, wherein a length of the longitudinal string is determined depending on an area of a lesion portion or a length of the stent.

11. The stent system, as set forth in claim 8, wherein lengths of the first and second longitudinal strings are determined depending on an area of a lesion portion or a length of the stent.

12. The stent system, as set forth in claim 8, wherein the longitudinal string passes, in a zigzag manner, through the film and mesh arranged in the longitudinal direction of the stent body.

13. The stent system, as set forth in claim 8, wherein the first and second longitudinal strings pass, in a zigzag manner, through the film and mesh arranged in the longitudinal direction of the stent body.

14. The stent system, as set forth in claim 8, wherein the drawstring is made of one of a medical fiber, a synthetic resin, a nonferrous metal, or a metal wire.

* * * * *